US008574468B1

(12) United States Patent
Davis et al.

(10) Patent No.: US 8,574,468 B1
(45) Date of Patent: Nov. 5, 2013

(54) BENZO-FUSED HETEROCYCLIC CHROMOPHORES FOR NONLINEAR OPTICAL DEVICES

(75) Inventors: Matthew C. Davis, Ridgecrest, CA (US); Andrew P. Chafin, Ridgecrest, CA (US); Geoffrey A. Lindsay, Ridgecrest, CA (US)

(73) Assignee: The United States of America as Represented by the Secretary of the Navy, Washington, DC (US)

( * ) Notice: Subject to any disclaimer, the term of this patent is extended or adjusted under 35 U.S.C. 154(b) by 0 days.

(21) Appl. No.: 13/556,868

(22) Filed: Jul. 24, 2012

Related U.S. Application Data

(63) Continuation of application No. 13/555,934, filed on Jul. 23, 2012.

(60) Provisional application No. 61/531,995, filed on Sep. 7, 2011.

(51) Int. Cl.
*F21V 9/04* (2006.01)
*F21V 9/06* (2006.01)
*G02B 5/22* (2006.01)
*G02B 5/26* (2006.01)
*G02F 1/03* (2006.01)
*G02F 1/07* (2006.01)

(52) U.S. Cl.
USPC ........... 252/587; 359/245; 359/279; 359/321; 359/326; 359/345; 385/131; 385/143; 427/162; 428/333; 528/330; 528/331

(58) Field of Classification Search
USPC .......... 252/582, 587; 359/252, 345, 245, 279, 359/321, 326; 385/131, 143; 427/162; 428/333; 528/330, 331
See application file for complete search history.

(56) References Cited

U.S. PATENT DOCUMENTS 6,348,992 B1    2/2002   Zhang et al.

OTHER PUBLICATIONS

Andrew P. Chafin, Matthew C. Davis, William W. Lai, Geoffrey A. Lindsay, Dong H. Park, Warren N. Herman,Benzofuran-terminated infrared dyes and their electro-optic properties in guest-host polymers.Optical Materials 33 (2011) 1307-1315.*
Matthew C. Davis, Thomas J. Groshens, and Damon A. Parrish, Preparation of cyan dyes from 6-Diethylaminobenzo[b]furan-2-carboxaldehyde, Synthetic Communications, 40: 3008-3020, 2010.*
Larry R. Dalton, Philip A. Sullivan, and Denise H. Bale, Electric Field Poled Organic Electro-optic Materials: State of the Art and Future Prospects, Chem. Rev. 2010, 110, 25-55, _ 2010 American Chemical Society.*
C. Zhang, et al, "Low $V\pi$ Electroopitc Modulators from CLD-1: Chromophore Design and Synthesis, Material Processing, and Characterization" Chem. Mater., 2001, 3043-3050, vol. 13.
Y. Enami, et al, "Hybrid cross-linkable polymer/sol-gel waveguide modulators with 0.65 V half wave voltage at 1550 nm" Appl. Phys. Lett., 2007, pp. 093505, vol. 91.

(Continued)

*Primary Examiner* — Bijan Ahvazi
(74) *Attorney, Agent, or Firm* — Charlene A. Haley

(57) ABSTRACT

A benzo-fused-heterocyclic elongated dye having a superior molecular hyperpolarizability and yet having an acceptably-low optical absorbance of light near 1550 nm in wavelength, which is an important optical communication band for telecommunication applications.

20 Claims, 3 Drawing Sheets

(56) References Cited

OTHER PUBLICATIONS

A. Chafin, et al, "A Pattern for Increasing the First Hyperpolarizability of a Push#Pull Polyene Dye as Indicated from DFT Calculations" J. Phys. Chem. C., 2008, pp. 7829-7835.

X. Ma, et al, "Toward highly efficient NLO chromophores" J. Mater. Chem, 2010, pp. 2369-2380, vol. 20.

L.R. Dalton, P.A. Sullivan, D.H. Bale, "Electric Field Poled Organic Electro-optic Materials: State of the Art and Future Prospects" Chem. Rev., 2010, pp. 25-55, vol. 110, No. 1.

A. Chafin, et al, "Benzofuran-terminated infrared dyes and their electro-optic properties in guest-host polymers" Optical Materials, 2011, pp. 1307-1315, vol. 33.

* cited by examiner

BENZO-FUSED HETEROCYCLIC CHROMOPHORES FOR NONLINEAR OPTICAL DEVICES

CROSS-REFERENCE TO RELATED APPLICATIONS

This is a continuation non-provisional application, claiming the benefit of, parent application Ser. No. 13/555,934 filed on Jul. 23, 2012, which also claim benefit to parent provisional patent application Ser. No. 61/531,995 filed on Sep. 7, 2011, whereby the entire disclosure of which is incorporated hereby reference.

STATEMENT REGARDING FEDERALLY SPONSORED RESEARCH OR DEVELOPMENT

The invention described herein may be manufactured and used by or for the government of the United States of America for governmental purposes without the payment of any royalties thereon or therefor.

FIELD OF THE INVENTION

The invention generally relates to organic nonlinear optical materials for electro-optic devices, and more specifically, to pentaenic chromophores that include a benzo-fused five-membered heterocyclic unit.

BACKGROUND OF THE INVENTION

Over the last twenty years, notable advancements to the science and technology of organic second-order nonlinear optical (NLO) materials have been made [see for example: L. R. Dalton, P. A. Sullivan, D. H. Bale, Chem. Rev. 2010, 110, 23-55]. Organic NLO materials are especially useful in electro-optic (EO) modulators as the active optical waveguide component [see for example: "Hybrid cross-linkable polymer/sol-gel waveguide modulators with 0.65 V half wave voltage at 1550 nm," Y. Enami, D. Mathine, C. T. DeRose, and R. A. Norwood, J. Luo, A. K.-Y. Jen, N. Peyghambarian, Optical Materials 2011, 33, 1307-1315]. EO modulators are used, for example, to transduce information from an electrical signal to an optical signal that can travel, for example, on optical fibers. EO modulators change (modulate) the phase and amplitude of an optical carrier signal by means of changing (modulating) the index of refraction of the optical waveguide material. The transduction of information is accomplished by applying the voltage of an electrical signal (carrying the data to be transduced to the optical signal) across the active optical waveguide. The index of refraction of the NLO material (also called the EO material) is changed in proportion to the intensity of the applied electric field, thereby changing the phase of the optical signal and also making possible the construction of an optical amplitude modulator based on interferometry. The index of refraction change of the EO material is based on the second-order nonlinear optical response (also called a three-wave mixing response), and involves only electronic motions in the dye. Thus, a distinguishing property of the organic three-wave mixing NLO materials is that the frequency of modulating (or speed of changing) its index of refraction may exceed 100 gigahertz (or be less than 0.1 nanosecond).

The electro-optic (EO) coefficient ($r_{33}$) is a well-known and useful figure-of-merit for comparing various NLO materials for use in EO modulators. The nomenclature "dye" and "chromophore" are used herein interchangeably. The dye is the key active component of the EO material. The dye has a long π-electron-conjugated backbone (also called the electronic conduit, and also called the charge-transfer conduit) that normally runs along the longest geometric axis of the dye. Dyes used in second-order NLO materials must be asymmetric, and they typically have an electron donor group on one end of the dye and an electron acceptor group on the other end of the dye. The magnitude of $r_{33}$ for films of these of high-bandwidth organic-dye-based EO materials is largely determined by the product of three molecular parameters (see Equation 1):

$$r_{33} \propto \beta N_d <\cos^3(\theta)> \qquad \text{Eq. (1)}$$

where β is the first molecular hyperpolarizability of the dye; $N_d$ is the molar concentration of dyes (the number density), and $<\cos^3(\theta)>$ is the polar order parameter (polar alignment) of the ensemble of dyes.

One common method to increase the polar order of the dyes in a film is to apply a large voltage across a film that has been heated near or above its glass transition temperature (Tg). Under those conditions, the ground-state dipole moments of the dyes align with the applied poling field, then the film is cooled to ambient (well below Tg) before the poling field is removed, which freezes in the polar order. The film can also be crosslinked during poling to freeze in the polar order.

The method of Density Functional Theory (DFT) is a practical desk-top computational tool for predicting the relative changes in β as a function of specific changes in the chemical structure of the dye molecule. DFT calculations (theoretical calculations) of β can be performed using the Gaussian03 program as described in reference [Optical Materials 2011, 33, 1307-1315]. DFT calculations also predict the dipole moment of the dye (μ). The dipole moment of the dye (μ) is also a useful quantity for comparing dyes, because very large dipole moments can be detrimental if the dipole-dipole repulsion between neighboring dyes lowers the overall polar alignment. This normally occurs when the dyes are packed closely together at high concentrations, for example, at $N_d > 10^{19}$ dye molecules per cubic centimeter.

A distinguishing chemical structure of the here-to-for best-performing type of dye used in EO modulators is the phenylene-tetraenic π-electron-conjugated backbone. Each "ene" group in the polyene backbone of the dye includes two methine atoms linked by a double bond (the methine atoms are sp2 hybridized). An ene unit is also called a vinylene unit. One type of here-to-for best-performing dye includes the 4-aminophenyl-tetraene-tricyanofuran molecular framework, in which an isophorone unit is used to rigidify (or ring-lock) the tetraenic backbone. This type of dye is called the "phenylene-tetraenic" dye or "phenyl-tetraenic" dye herein. Examples of early publication are: U.S. Pat. No.

6,348,992 and Cheng Zhang and Larry R. Dalton, Min-Cheol Oh, Hua Zhang, and William H. Steier, *Chem. Mater.* 2001, 13, 3043-3050.

Another type of phenyl-tetraenic dye includes the 4-aminophenyl-(2,5-divinylene-heterocyclodiene)-tricyanofuran molecular framework. For example, see: X. Ma, F. Ma, Z. Zhao, N. Song, J. Zhang, *J. Mater. Chem.* 2010, 20, 2369-2380. These dyes are also considered here-to-fore among the best performing dyes for use in electro-optic modulators. Examples of heterocyclodienes are thiophene, pyrrole, thiazole and similar heterocyclic rings that include two ene groups. Thus, the 2,5-divinylene-thiophene is a tetraenic backbone unit.

A known strategy for increasing the β of organic dyes is to increase the length of the π-electron conjugated backbone (the electronic conduit) of the dye by adding another ene unit, for example, making the dye a pentaenic dye. However, increasing the length of the π-electron conjugated conduit of the well-known phenylene-tetraenic dyes has invariably resulted in dyes that exhibit increased and unacceptable optical absorption in the ~1550 nm device operating window. This is because adding one more ene group extends the low-energy side of the electronic absorption envelop (the red tail). The problem arises when the red-tail wavelengths extends into and overlap with the 1550 nm optical carrier signal, which leads to unacceptable optical absorption loss. For the Mach-Zehnder modulator, the typical upper limit for acceptable optical propagation loss is ~0.25 dB/mm, which also sets the upper limit on concentration of the dye in the film (and thus the upper limit on $r_{33}$), which is a well-known trade-off. Furthermore, red-shifting of the tail of the electronic absorption spectrum to wavelengths greater than 1550 nm increases the rate of detrimental photo-chemical reactions. The near-infrared (NIR) attenuation caused by the dyes in an optical waveguide (at least for relative comparisons) can be estimated by measuring the optical absorption of a solution of known concentration of dye as a function of optical wavelength using a conventional ultraviolet-visible (UV-Vis) spectrometer.

Another known strategy for increasing the β of organic dyes is the incorporation of strong (relative to hydrogen) electron-withdrawing and strong (relative to hydrogen) electron-donating groups on the internal methines of large dyes. Methines are the sp2 carbons, and other hetero sp2 atoms, that make up the π-conjugated conduit of the dye. DFT computations have shown that β is usually enhanced when electron-withdrawing groups (W) are attached to even-numbered (e) internal methine carbons and electron-donating groups (D) are attached to odd-numbered (o) internal methines, the so-called eW/oD pattern. The methine numbering system for the dyes used herein is the same numbering system used in this reference: A. P. Chafin, G. A. Lindsay, *J. Phys. Chem. C* 2008, 112, 7829-7835.

Bulky, steric-hindering groups attached to the dye are needed to prevent aggregation and crystallization of large dyes at high loadings (at high concentrations). Attachment of large groups, such as t-butyldiphenylsiloxy, diphenylmethylsiloxy and similar-sized groups, to the ends and mid-section of the dye is a well-known method for improving solubility of the dyes. Attaching to the dye several linear or branched alkyl groups that include two to eight carbon atoms is also a well-known method for improving solubility of dyes. Such large groups are considered to be one type of "functionalized group," a terminology used herein.

It is to be understood that the foregoing is exemplary and explanatory only and are not to be viewed as being restrictive of the invention, as claimed. Further advantages of this invention will be apparent after a review of the following detailed description of the disclosed embodiments, which are illustrated schematically in the accompanying drawings and in the appended claims.

Figure 1A:
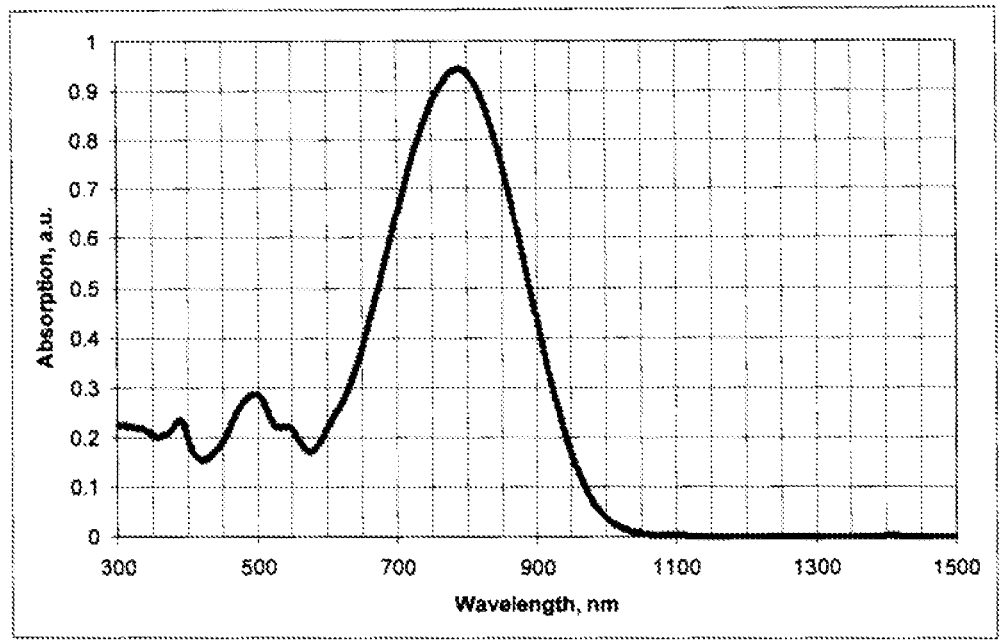
FIGS. 1*a-b* are graphs of examples of dyes from Example 16 and Example 21, according to embodiments of the invention.

It is to be understood that the foregoing general description and the following detailed description are exemplary and explanatory only and are not to be viewed as being restrictive of the invention, as claimed. Further advantages of this invention will be apparent after a review of the following detailed description of the disclosed embodiments, which are illustrated schematically in the accompanying drawings and in the appended claims.

DETAILED DESCRIPTION OF THE EMBODIMENTS OF THE INVENTION

Embodiments of the invention generally relate to organic nonlinear optical materials for use in electro-optic devices, and, more specifically, to pentaenic chromophores including a benzo-fused five-membered heterocyclic unit resulting in marked increase in molecular hyperpolarizability (β), and yet the new chromophores do not suffer additional optical absorption in the 1530 nm to 1570 nm optical communication window.

Embodiments of the invention describe a class of superior pentaenic dye compositions for use in optical waveguides operating with a NIR light source, for example, operating at 1550 nm (this light becomes the information carrier signal). Embodiments of this invention increase the β of the chromophore by the incorporation of an additional ene unit to the π-conjugated backbone by means of a benzo-fused five-membered heterocyclic unit (the BFFH unit). These superior elongated dyes are hereafter called BFFH dyes.

Surprisingly, in addition to increasing the β, the incorporation of the benzo-fused five-member heterocyclic unit also reduces or eliminates the red-shift in the near infrared (NIR) portion of the ultraviolet-visible-NIR absorption spectrum that has been here-to-fore practically unavoidable when lengthening the charge-transfer conduit of the dye. The BFFH unit also rigidifies the polyene conduit, which may further enhance the β and the stability of the dye.

Another embodiment of this invention is the placement of heteroatoms in the BFFH unit in the beneficial eW/oD pattern [see A. P. Chafin, G. A. Lindsay, J. Phys. Chem. C 112 (2008) 7829-7835]. Simple DFT calculations were performed on BFFH dye structures of embodiments of the invention to confirm the benefits of the eW/oD pattern, and to contrast the BFFH dyes with a few well-known phenylene-tetraenic dyes. The superior properties predicted for the dyes of embodiments of the invention are shown in Table 1. The effects of various internal substituents on the dyes are also compared. The numbering scheme identifies the methine (the sp2-hybridized atomic) positions along the polyene conduit to which the substituents (groups) are attached or incorporated.

TABLE 1

A comparison of various dyes of interest for EO modulators
(molecular properties calculated by simple DFT)

Phenylene dye:

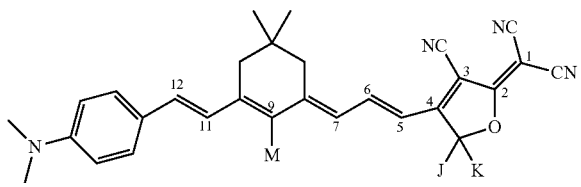

BFFH dye:

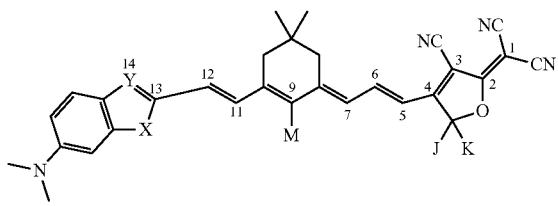

| Dye type | X #13 | Y #14 | M #9 | J #4 | K #4 | $\beta_{\mu 0}$ $10^{-30}$ esu | $\mu$ Debye | $\phi$ degrees |
|---|---|---|---|---|---|---|---|---|
| Phenylene-1 | — | — | H | CH₃ | CH₃ | 690 | 23.1 | 16 |
| Phenylene-2 | — | — | OCH₃ | CH₃ | CH₃ | 720 | 22.8 | 17 |
| Phenylene-3 | — | — | H | CF₃ | phenyl | 768 | 23.7 | 14 |
| Phenylene-4 | — | — | OCH₃ | CF₃ | phenyl | 799 | 23.5 | 16 |
| Phenylene-5 | — | — | SCH₃ [17] | CF₃ | phenyl | 774 | 23.4 | 16 |
| BFFH-1 | O | CH | H | CH₃ | CH₃ | 980 | 22.3 | 14 |
| BFFH-2 | O | CH | OCH₃ | CH₃ | CH₃ | 1092 | 21.6 | 14 |
| BFFH-3 | S | CH | OCH₃ | CH₃ | CH₃ | 1153 | 22.1 | 14 |
| BFFH-4 | NAc | CH | OCH₃ | CH₃ | CH₃ | 1206 | 20.3 | 20 |
| BFFH-5 | NCH₃ | CH | OCH₃ | CH₃ | CH₃ | 1215 | 22.5 | 20 |
| BFFH-6 | O | N | OCH₃ | CH₃ | CH₃ | 1133 | 19.5 | 23 |
| BFFH-7 | S | N | OCH₃ | CH₃ | CH₃ | 1157 | 20.1 | 21 |
| BFFH-8 | NCH₃ | N | OCH₃ | CH₃ | CH₃ | 1266 | 20.8 | 26 |
| BFFH-9 | O | CH | H | CF₃ | phenyl | 1025 | 22.8 | 17 |
| BFFH-10 | O | CH | Morpholino | CF₃ | phenyl | 1165 | 21.7 | 14 |
| BFFH-11 | O | CH | OCH₃ | CF₃ | phenyl | 1213 | 22.2 | 12 |
| BFFH-12 | NCH₃ | CH | OCH₃ | CF₃ | phenyl | 1312 | 23.3 | 17 |
| BFFH-13 | O | N | OCH₃ | CF₃ | phenyl | 1325 | 19.5 | 20 |
| BFFH-14 | NCH₃ | N | H | CF₃ | CH₃ | 1168 | 21.6 | 25 |
| BFFH-15 | S | N | OCH₃ | CF₃ | phenyl | 1377 | 20.3 | 18 |
| BFFH-16 | NCH₃ | N | OCH₃ | CF₃ | phenyl | 1440 | 21.1 | 25 |

All of the dyes discussed herein include a variously-substituted tricyanodihydrofuran (TCF) terminal electron-accepting group, which is on the right side of the dye structures shown in Table 1 that includes methine positions 1, 2, 3, and 4. The dye structures and calculated values shown in Table 1 are for the TCF group being in the 4,5-Z conformation. Furthermore, it should be noted that the electron-donating side of the dye (on the left side of the dye structures shown in Table 1) in every case includes an amino group in the 4-position of the BFFH unit (ether and thio groups are also acceptable electron donating groups). The same is true for the phenylene unit in the Phenylene dyes, namely, the 4-position includes the electron-donating group.

When using DFT calculations to compare and contrast various dyes, the $\beta_{\lambda 0}$ is an appropriate quantity to use as a figure of merit. The $\beta_{\mu 0}$, equals $\beta_0 \cos(\phi)$, where $\phi$ is the angle between the $\beta_0$ vector and the ground-state dipole moment vector of the dye ($\mu$). Herein, the symbol $\beta$ will be understood to be referring to $\beta_{\mu 0}$.

Many of the BFFH dyes are also predicted to have a slightly smaller dipole moment ($\mu$), as shown in Table 1, in contrast to the phenylene dyes, which should lead to less dipole-dipole repulsion at high loadings, and hence, a higher degree of polar alignment.

Referring to Table 1, according to DFT calculations, an electron-donating group placed in the #13 position (X) of the BFFH dyes can enhance $\beta_{\mu 0}$. When X is ether (oxygen), as is the case for BFFH-1 and BFFH-2, these so-called benzofuran dyes are predicted to have 40 to 50% improvement in $\beta_{\mu 0}$ over their respective phenylene-tetraenic dye analogues (Phenylene-1 and Phenylene-2). Other types of X groups, including amide, and functionalized amide are within the scope of the embodiments of the invention.

In the BFFH dyes, an azomethine (—N=) in the #14 position (Y), compared to a carbon methine (—CR=), where R is hydrogen, is predicted to enhance $\beta_{\mu 0}$. In fact, the BFFH-16 dye including the benzimidazole ring is predicted by DFT to have a $\beta_{\mu 0}$ that is nearly two-times larger than that of the analogous state-of-the-art phenylene-tetraenic dyes (including Phenylene-4 dye in Table 1). Other types of Y groups (atoms in the #14 position) within the scope of embodiments of the invention are, for example, atoms that are sp2-hybridized (that have sp2 molecular orbitals), including phosphorous (and functionalize phosphorous).

In the structures above Table 1, the J and K groups attached to the TCF group are shown as methyl groups. Additional J and K groups are also contemplated for embodiments of the invention, including larger alkyl, aryl, functionalized alkyl, and functionalized aryl groups. When considering functionalized groups to select for J or K, when one chooses an electron-accepting group, such as, for example, the trifluoromethyl group, then, in contrast to the methyl group, the DFT calculations predict an enhancement to $\beta_{\mu 0}$. Electron-withdrawing groups attached to the #4 methine position on the BFFH dyes are predicted to be beneficial. One can also use other types of functional groups on J and K, including hydroxyl and carboxyl, in order for the dye to be attached to other groups that would increase the solubility of the dye. Functional groups also afford the option of attaching the dye to the solid organic matrix that makes up the bulk of the optical-waveguide film, thereby increasing the mechanical stability of the dye by hindering rotationally diffusion at elevated temperatures and maintaining polar alignment.

Placing an electron-donating group (M) on the #9 position is predicted by DFT to enhance $\beta_{\mu 0}$. The morpholino (and the dimethylamino) group on the #9 position (BFFH-10) are predicted to enhance $\beta$ (in contrast to hydrogen) but to be slightly less enhancing than the methoxy group. The fluorine atom attached directly to an odd-numbered methine carbon, including the #9 position in the π-electron conduit of the dye, is predicted by DFT calculations to increase $\beta$ (presumably due to its inductive electron-donating effect). However, this would not be the case for a trifluoromethyl group and most other electron-withdrawing groups. Additional M groups are contemplated for embodiments of the invention including, but not limited to, hydrogen, alkyl, aryl, alkoxy, aryloxy, t-butyldiphenylsiloxy, diphenylmethylsiloxy, dialkyl amine, diaryl amine, alkyaryl amine, amide, functionalized alkyl, functionalized aryl, functionalized alkoxy, functionalized aryloxy, functionalized dialkyl amine, functionalized diaryl amine, functionalized alkyaryl amine, functionalized amide and other functionalized groups. The functional groups may be included to improve solubility of the dye and to attach the dye to the solid matrix that makes up the optical waveguide film.

The molecular structures of the BFFH dyes shown above Table 1 have methyl groups attached to the terminal amine electron-donating group (left end of the dye); however, it is often advantageous to attach larger alkyl groups, larger aryl groups, and functionalized alkyl and functionalized aryl groups to that amine. The larger groups add bulk and steric hindrance, which improves the solubility of the dye and prevent aggregation and crystallization. The functional groups can include a reactive group, including, but not limited to, a hydroxyl group or a carboxyl group, by which the dye can be chemically attached to polymers, to other bulky groups, to dendrimers, and the like. For the case of functionalized groups attached to the terminal amine donating group, one would typically avoid electron-withdrawing functionalized groups, including fluorinated alkyl groups, when one needs to maximize the molecular hyperpolarizability of the dye.

When these chromophores are in the form of a processed film in a device, they must remain soluble (in solid solution). The chromophores should not aggregate nor crystallize under the conditions of device operation and storage, because any density fluctuations in the film (in the optical waveguide), including crystallites that are large enough to scatter near-infrared light, will cause loss of optical power in the waveguide. Light scattering out of the optical waveguide may limit the usefulness of the device. Complete solubility of the dye is normally achieved by attaching the appropriate number and size of bulky groups to the chromophore. The selection of number and size of bulky groups is often a trial and error procedure. To prevent aggregation, the chromophores can also be attached in a large superstructure or matrix by various means, including, but not limited to, in a polymerized form, a dendrimeric form, a star form, an oligomeric form, a branched macromolecular form, and a crosslinked sol-gel form.

The near-infrared light passing through the nonlinear optical film, including light from light-emitting diodes that are an integral part of the optical waveguide device, is normally nearly monochromatic, and is typically in the wavelength range of 1530 nm to 1570 nm, one of the common EO-device communications windows. Light sources are contemplated that emit at wavelengths ranging out to 3000 nm. However, one would normally avoid sources that emit more than ten percent of their light at wavelengths in the electromagnetic spectrum that are strongly absorbed by the organic materials that are used to construct the NLO waveguide (and to construct the optical cladding materials).

In a nonlinear optical device (an electro-optic device), light is normally guided in a so-called core of the waveguide. The core includes the chromophores of this embodiment of the invention. The core is normally sandwiched between (or surrounded by) optical claddings that have a lower index of refraction than the core. However, other waveguide constructs are contemplated, such as the case in which some amount of chromophore is placed in at least one of the claddings.

The chromophores of the embodiments of the invention, for a given concentration of dye, provide a higher electro-optic coefficient for a given acceptable optical absorption in the 1530-1570 nm communications window than has previously been reported. This combination of properties affords the device constructor the option of constructing a smaller device, using a lower operating voltage, and/or measuring a weaker electric field with the device than has previously been possible.

The EO coefficient of the active optical waveguide is increased by using a higher concentration of dye molecules in the waveguide. One would typically like to make a core waveguide with at least $5 \times 10^{18}$ dye molecules per cubic centimeter (N), and when possible, as high as $5 \times 10^{21}$. The upper limit of the concentration, however, is determined by the size of the chromophore including the volume of all of the groups attached to it, which determines many chromophores can be packed inside a cubic centimeter of NLO material. However, when the dye tends to form aggregates (crystallites), the maximum useful concentration will normally be below the concentration at the onset of aggregation. A properly constructed dye molecule will not aggregated at the highest possible packing concentration. The maximum concentration of dye will obviously be limited to a concentration below the concentration where there is an intolerable amount of optical absorption loss in the optical waveguide. The maximum tolerable optical absorption loss is usually about 0.25 dB/mm of waveguide path length, but the actual number will be dictated by the actual device specifications for each application.

Applications and uses for the chromophores of the embodiments of the invention are any of the normal device applications that require an electro-optic material. However, it is anticipated that new applications may be afforded by the advanced performance of these chromophores.

The invention generally relates to chromophore(s), including: the base formula A;

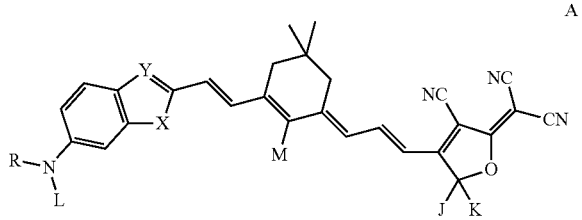

A where X is selected from the group consisting of methylene, oxygen, sulfur, alkyl amine, amide, functionalized methylene, functionalized amine, and functionalized amide; where Y is selected from the group consisting of carbon methine, functionalized carbon methine, azamethine, and atoms forming sp2-hybridized molecular orbitals; where M is selected from the group consisting of hydrogen, fluorine, alkyl, aryl, alkoxy, aryloxy, t-butyldiphenylsiloxy, alkyl amine, morpholine, aryl amine, alkyaryl amine, amide, functionalized alkyl, functionalized aryl, functionalized alkoxy, functionalized aryloxy, functionalized alkyl amine, functionalized aryl amine, functionalized alkyaryl amine, and functionalized amide; where J and K are independently selected from the group consisting of alkyl, aryl, functionalized alkyl, fluorine-functionalized alkyl, functionalized aryl, and fluorine-functionalized aryl; and where R and L are independently selected from the group consisting of alkyl, aryl, functionalized alkyl, and functionalized aryl.

In embodiments, the chromophore includes X is oxygen and Y is carbon methine. In other embodiments, X is alkyl amine, Y is azamethine, and M is hydrogen or alkyl. In yet other embodiments, X is alkyl amine and Y is carbon methine. Yet in other embodiments, X is sulfur and Y is carbon methine.

In other embodiments include amorphous nonlinear optical material(s), having: at

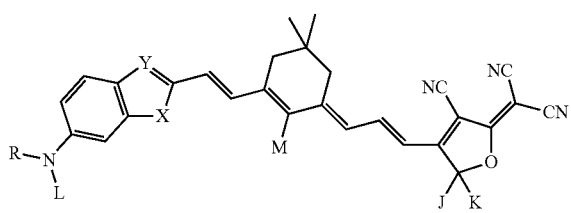

B least one chromophore having the base formula B; where X is selected from the group consisting of methylene, oxygen, sulfur, alkyl amine, amide, functionalized methylene, functionalized amine, and functionalized amide; where Y is selected from the group consisting of carbon methine, functionalized carbon methine, azamethine, and atoms forming sp2-hybridized molecular orbitals; where M is selected from the group consisting of hydrogen, fluorine, alkyl, aryl, alkoxy, aryloxy, t-butyldiphenylsiloxy, alkyl amine, morpholine, aryl amine, alkyaryl amine, thioalkyl, thioaryl, amide, functionalized alkyl, functionalized aryl, functionalized alkoxy, functionalized aryloxy, functionalized alkyl amine, functionalized aryl amine, functionalized alkyaryl amine, and functionalized amide; where J and K are independently selected from the group consisting of alkyl, aryl, functionalized alkyl, fluorine-functionalized allyl, functionalized aryl, and fluorine-functionalized aryl; where R and L are independently selected from the group consisting of alkyl, aryl, functionalized alkyl, and functionalized aryl; and where the concentration of the chromophore in the nonlinear optical material is greater than about $10^{18}$ molecules per cubic centimeter.

In embodiments, the concentration of chromophore in the nonlinear optical material is less than the concentration at which infrared light in the wavelength range of 1530 nm to 1570 nm becomes attenuated by more than about 0.25 decibels per millimeter of the nonlinear optical material. In embodiments, X is oxygen and Y is carbon methine. In other embodiments, X is alkyl amine, Y is azamethine, and M is hydrogen or alkyl. Yet in other embodiments, X is alkyl amine and Y is carbon methine.

In other embodiments, the electro-optical device(s) are including: at least one nonlinear optical material including at least one soluble chromophore having the base formula C;

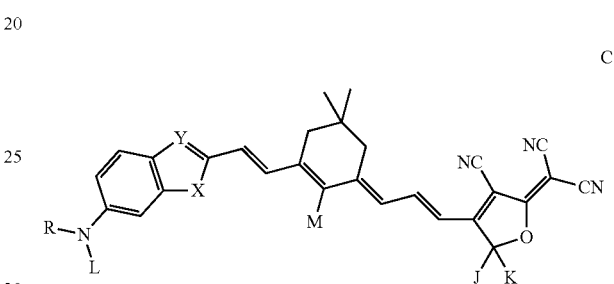

C where X is selected from the group consisting of methylene, oxygen, sulfur, alkyl amine, amide, functionalized methylene, functionalized amine, and functionalized amide; where Y is selected from the group consisting of carbon methine, functionalized carbon methine, azamethine, and atoms capable of forming sp2-hybridized molecular orbitals; where M is selected from the group consisting of hydrogen, fluorine, alkyl, aryl, alkoxy, aryloxy, butyldiphenylsiloxy, alkyl amine, morpholine, aryl amine, alkyaryl amine, amide, functionalized alkyl, functionalized aryl, functionalized alkoxy, functionalized aryloxy, functionalized alkyl amine, functionalized aryl amine, functionalized alkyaryl amine, and functionalized amide; where J and K are independently selected from the group consisting of alkyl, aryl, functionalized alkyl, fluorine-functionalized alkyl, functionalized aryl, and fluorine-functionalized aryl; where R and L are independently selected from the group consisting of alkyl, aryl, functionalized alkyl, and functionalized aryl; and where the concentration of the chromophore in the nonlinear optical material is greater than about $10^{18}$ molecules per cubic centimeter.

In embodiments, the concentration of chromophore in the nonlinear optical material is less than the concentration at which infrared light in the wavelength range of 1530 to 1570 nm becomes attenuated by more than about 0.25 decibels per millimeter of the nonlinear optical material. In embodiments, X is oxygen and Y is carbon methine. In other embodiments, X is alkyl amine, Y is azamethine, and M is hydrogen or alkyl. Yet in other embodiments, X is alkyl amine and Y is carbon methine.

Yet in other embodiments, the electro-optical device(s) are including: at least one optical waveguide core formed by electric-field poling and including at least one soluble chromophore having the base formula D;

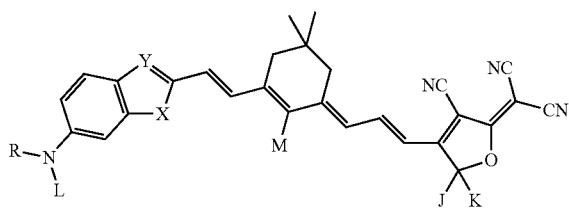

D where X is selected from the group consisting of methylene, oxygen, sulfur, alkyl amine, amide, functionalized methylene, functionalized amine, and functionalized amide; where Y is selected from the group consisting of carbon methine, functionalized carbon methine, azamethine, and atoms capable of forming sp2-hybridized molecular orbitals; where M is selected from the group consisting of hydrogen, fluorine, alkyl, aryl, alkoxy, aryloxy, t-butyldiphenylsiloxy, alkyl amine, morpholine, aryl amine, alkyaryl amine, amide, functionalized alkyl, functionalized aryl, functionalized alkoxy, functionalized aryloxy, functionalized alkyl amine, functionalized aryl amine, and functionalized amide; where J and K are independently selected from the group consisting of alkyl, aryl, functionalized alkyl, fluorine-functionalized alkyl, functionalized aryl, and fluorine-functionalized aryl; where R and L are independently selected from the group consisting of alkyl, aryl, functionalized alkyl, and functionalized aryl; and where the concentration of the chromophore in the nonlinear optical material is greater than about $10^{18}$ molecules per cubic centimeter. In embodiments, the concentration of the chromophore in the nonlinear optical material is less than the concentration at which infrared light in the wavelength range of 1530 to 1570 nm becomes attenuated by more than about 0.25 decibels per millimeter of the nonlinear optical material. In embodiments, X is oxygen and Y is carbon methine. IN other embodiments, X is alkyl amine, Y is azamethine, and M is hydrogen or alkyl. Yet in other embodiments, X is alkyl amine and Y is carbon methine.

Another aspect of the invention includes chromophore(s) having: the base formula E;

E

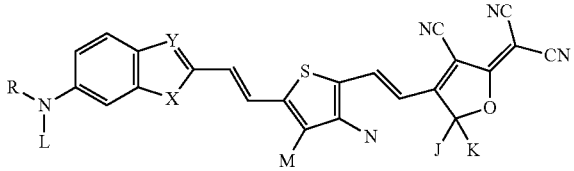

where X is selected from the group consisting of methylene, oxygen, sulfur, alkyl amine, amide, functionalized methylene, functionalized amine, and functionalized amide; where Y is selected from the group consisting of carbon methine, functionalized carbon methine, azamethine, and atoms forming sp2-hybridized molecular orbitals; where M and N are independently selected from the group consisting of hydrogen, fluorine, alkyl, aryl, alkoxy, aryloxy, t-butyldiphenyl siloxy, functionalized alkyl, functionalized aryl, functionalized alkoxy, functionalized aryloxy, and functionalized amide; where J and K are independently selected from the group consisting of alkyl, aryl, functionalized alkyl, fluorine-functionalized alkyl, functionalized aryl, and fluorine-functionalized aryl; and wherein R and L are independently selected from the group consisting of alkyl, aryl, functionalized alkyl, and functionalized aryl.

In embodiments, X is oxygen, Y is carbon methine, M and N are independently selected from alkyl, alkoxy and hydrogen. In other embodiments, X is alkyl amine and Y is azamethine. In yet other embodiments, X is alkyl amine and Y is carbon methane. In other embodiments, X is sulfur and Y is carbon methine.

Embodiments of the invention generally relate to amorphous nonlinear optical material(s) having: at least one chromophore having the base formula F;

F

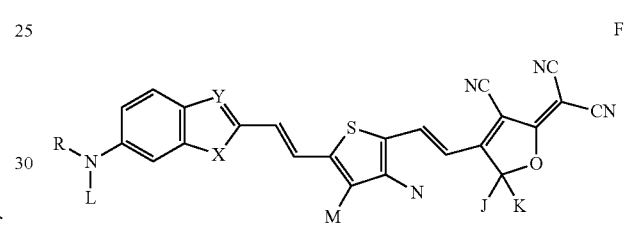

where X is selected from the group consisting of methylene, oxygen, sulfur, amine, amide, functionalized methylene, functionalized amine, and functionalized amide; where Y is selected from the group consisting of carbon methine, functionalized carbon methine, azamethine, and atoms forming sp2-hybridized molecular orbitals; where M and N are independently selected from the group consisting of hydrogen, fluorine, alkyl, aryl, alkoxy, aryloxy, t-butyldiphenyl siloxy, functionalized alkyl, functionalized aryl, functionalized alkoxy, functionalized aryloxy, and functionalized amide; where J and K are independently selected from the group consisting of alkyl, aryl, functionalized alkyl, fluorine-functionalized alkyl, functionalized aryl, and fluorine-functionalized aryl; where R and L are independently selected from the group consisting of alkyl, aryl, functionalized alkyl, and functionalized aryl; and where the concentration of the chromophore in the nonlinear optical material is greater than about $10^{18}$ molecules per cubic centimeter. In embodiments, the concentration of chromophore in the nonlinear optical material is less than the concentration at which infrared light in the wavelength range of 1530 to 1570 nm becomes attenuated by more than about 0.25 decibels per millimeter of the nonlinear optical material. In embodiments, X is oxygen and Y is carbon methine. In other embodiments, X is alkyl amine and Y is azamethine. In other embodiments, X is alkyl amine and Y is carbon methine.

In other embodiments, the invention generally relates to electro-optical device, comprising: at least one nonlinear optical material including at least one soluble chromophore having the base formula G;

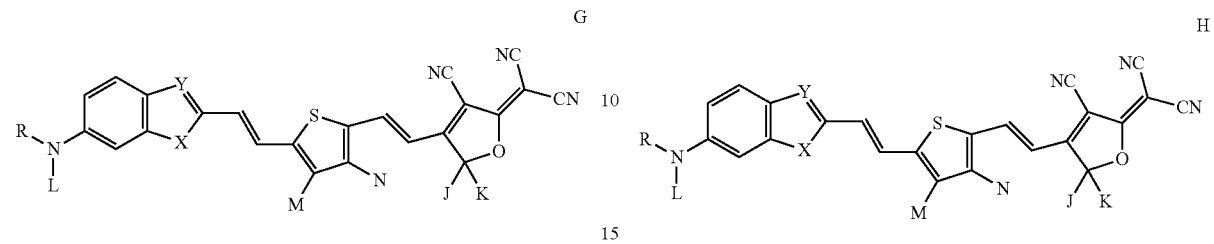

where X is selected from the group consisting of methylene, oxygen, sulfur, amine, amide, functionalized methylene, functionalized amine, and functionalized amide; where Y is selected from the group consisting of carbon methine, functionalized carbon methine, azamethine, and atoms capable of forming sp2-hybridized molecular orbitals; where M and N are independently selected from the group consisting of hydrogen, fluorine, alkyl, aryl, alkoxy, aryloxy, t-butyldiphenylsiloxy, functionalized alkyl, functionalized aryl, functionalized alkoxy, functionalized aryloxy, and functionalized amide; where J and K are independently selected from the group consisting of alkyl, aryl, functionalized alkyl, and functionalized aryl; fluorine-functionalized alkyl, functionalized aryl, and fluorine-functionalized aryl; where R and L are independently selected from the group consisting of alkyl, aryl, functionalized alkyl, fluorine-functionalized alkyl, functionalized aryl, and fluorine-functionalized aryl; and where the concentration of chromophore in the nonlinear optical material is greater than about $10^{18}$ molecules per cubic centimeter. In embodiments, the concentration of chromophore in the nonlinear optical material is less than the concentration at which infrared light in the wavelength range of 1530 to 1570 nm becomes attenuated by more than about 0.25 decibels per millimeter of the nonlinear optical material. In embodiments, X being oxygen and Y being carbon methane. In other embodiments, X is alkyl amine, Y is azamethine, M is hydrogen, and N is hydrogen. In other embodiments, X is alkyl amine and Y is carbon methine.

Yet another embodiment relates to electro-optical device(s) having: at least one optical waveguide core formed by electric-field poling and including at least one soluble chromophore having the base formula H;

where X is selected from the group consisting of methylene, oxygen, sulfur, amine, amide, functionalized methylene, functionalized amine, and functionalized amide; where Y is selected from the group consisting of carbon methine, functionalized carbon methine, azamethine, and atoms capable of forming sp2-hybridized molecular orbitals; where M and N are independently selected from the group consisting of hydrogen, fluorine, alkyl, aryl, alkoxy, aryloxy, t-butyldiphenylsiloxy, functionalized alkyl, functionalized aryl, functionalized alkoxy, functionalized aryloxy, and functionalized amide; where J and K are independently selected from the group consisting of alkyl, aryl, functionalized alkyl, fluorine-functionalized alkyl, functionalized aryl, and fluorine-functionalized aryl; where R and L are independently selected from the group consisting of alkyl, aryl, functionalized alkyl, and functionalized aryl; and where the concentration of chromophore in the nonlinear optical material is greater than about $10^{18}$ molecules per cubic centimeter.

In embodiments, the concentration of chromophore in the nonlinear optical material is less than the concentration at which infrared light in the wavelength range of 1530 to 1570 nm becomes attenuated by more than about 0.25 decibels per millimeter of the nonlinear optical material. In embodiments, X is oxygen and Y is carbon methine. In other embodiments, X is alkyl amine and Y is azamethine. Yet in other embodiments, X is alkyl amine and Y is carbon methine.

Working Examples 1-20 below include the synthetic steps involved in preparing three benzofuran dyes (similar to the BFFH-1, -10, and -11 dyes shown in Table 1). Typical chemical structures of precursors to the first example dye and the preparation methods for the precursors and the dye are outlined in Scheme 1 shown directly below (also see *Synthetic Communications* 2010, 40, 3008-3020).

Scheme 1.

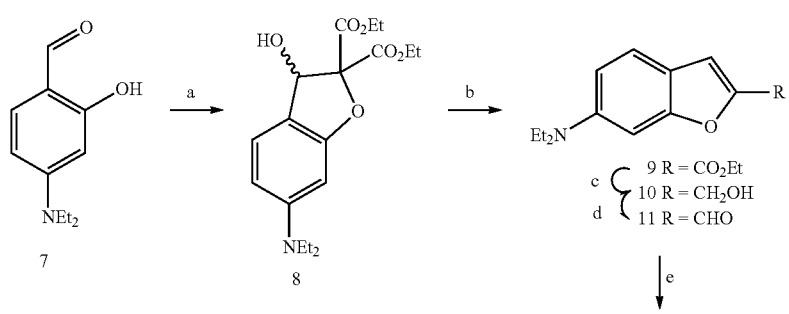

-continued

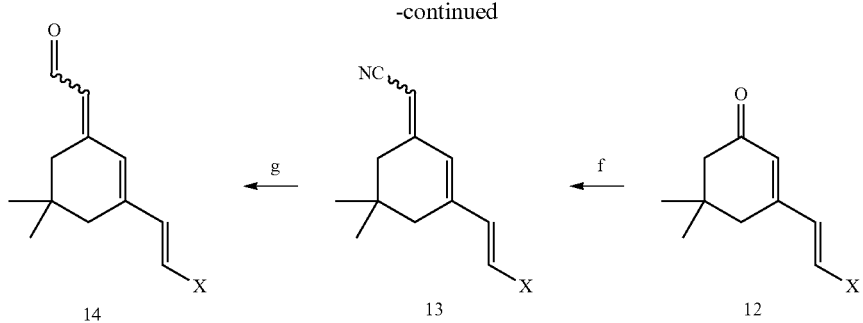

14  13  12

X = 6-diethylaminobenzo[b]furan-2-yl

Reagents and conditions: a) KOtBu, diethyl bromomalonate, DMF; b) PPA, 100° C.;
c) LAH, THF; d) p-chloranil, CHCl₃, 40° C.; e) isophorone, NaOH, H₂O, EtOH;
f) 1. MeCN, LDA, THF, -78° C., 2. HOAc, reflux; g) 1. DIBAL, PhMe, -78° C.
2. H₂O, SiO₂, oxalic acid, rt.

Example 1

The preparation of racemic diethyl 3-hydroxy-6-diethylamino-2,3-dihydrobenzo[b]furan-2,2-dicarboxylate, compound 8 in Scheme 1. A 1-L round-bottomed flask equipped with mechanical stirrer and internal thermometer was charged with 400 mL anhydrous dimethylformamide (DMF) and 50 g of compound 7 (0.26 mol) were added. An endotherm of 7° C. occurred while the solids dissolved. The solution was then cooled to 5° C. with an ice bath. In one portion, 32 g KOtBu (0.286 mol, 1.1 equiv) was added, and the temperature climbed to 20° C. then slowly fell back to 10° C. After 5 min, the potassium salt of the 4-diethylaminosalicylaldehyde precipitated. In a gentle stream, 74.57 g diethyl bromomalonate (0.312 mol, 1.2 equiv) was added using an addition funnel over 15 min. After ~10 g of the bromide had been added, the solids broke up and stirring resumed. The temperature peaked at 29° C., and the cooling bath was removed. The mixture was stirred at rt for 1 h The mixture was poured into 2 L distilled H₂O including 16.42 mL glacial HOAc (0.286 mol, 1.1 equiv). A brown oil separated initially and after stirring for several hours became a tan solid. The crude product was collected on a coarse-porosity glass frit. The title compound was obtained as white microcrystals from hexanes/EtOAc (75 g, 83%). Mp 87-89° C. dH (CDCl₃): 7.19 (d, $J$=9.1 Hz, 1H), 6.33-6.27 (m, 2H), 5.79 (d, $J$=8.3 Hz, 1H), 4.43-4.14 (m, 4H), 3.32 (q, $J$=7.1 Hz, 4H), 2.22 (d, $J$=8.4 Hz, OH), 1.32 (t, $J$=7.1 Hz, 3H), 1.28 (t, $J$=7.2 Hz, 3H), 1.14 (t, $J$=7.1 Hz, 6H); dC (CDCl₃): 166.77, 165.73, 160.83, 150.93, 126.15, 112.3, 106.29, 93.89, 93.38, 62.64, 62.56, 44.84, 14.23, 14.07, 12.59. Elemental analysis calculated for $C_{18}H_{25}H_{25}NO_6$: C, 61.52; H, 7.17; N, 3.99. Found: C, 61.62; H, 7.22; N, 3.97.

Example 2

The preparation of ethyl 6-diethylaminobenzo[b]furan-2-oate, compound 9 in Scheme 1. A 1-L beaker was charged with 410 g polyphosphoric acid (PPA) followed by 81.9 g compound 8 (0.23 mol). The mixture was heated on a hotplate to 100° C. and mechanically stirred with a steel spatula by hand. The color became bright yellow, and gas that evolved caused foaming. After 30 min, the yellow color noticeably changed to tan, and 1H NMR of an aliquot of the reaction mixture dissolved in DMSO-d6 showed that all the starting material was consumed and the reaction was complete. Water (1 L) was added, and the mixture was dissolved to give a clear solution. The mixture was transferred to a 3-L beaker, magnetically stirred, and cooled in an ice bath while a previously prepared, cold solution of 205 g NaOH dissolved in 1 L H₂O was added in a gentle stream. Care was taken to keep the internal temperature below 20° C. to prevent ester hydrolysis. The resulting pH was ~5 and a brown oil separated. The mixture was extracted twice with 500-mL portions of Et₂O. After drying over anhydrous MgSO₄, the solution was evaporated to half the volume and diluted with an equal volume of hexanes. The mixture was filtered through SiO₂ to remove some polar impurities. Evaporation of the filtrate gave the title compound as a pale yellow oil (51.6 g, 86%). No further purification was performed. dH (CDCl₃): 7.43 (dd, $J$=8.9 and 0.6 Hz, 1H), 7.40 (d, $J$=1.0 Hz, 1H), 6.77 (m, 1H), 6.74 (dd, $J$=8.7 and 2.3 Hz, 1H), 4.40 (q, $J$=7.2 Hz, 2H), 3.41 (q, $J$=7.0 Hz, 4H), 1.40 (t, $J$=7.2 Hz, 3H), 1.19 (t, $J$=6.9 Hz, 6H); dC (CDCl₃): 159.62, 158.48, 148.46, 142.79, 122.80, 115.84, 114.38, 110.55, 92.93, 60.62, 44.72, 14.25, 12.26. Elemental analysis calculated for $C_{15}H_{19}NO_3$: C, 68.94; H, 7.33; N, 5.36. Found: C, 70.01; H, 7.40, 5.33.

Example 3

The preparation of 2-hydroxymethyl-6-diethylaminobenzo[b]furan, compound 10 in Scheme 1. A 1-L round-bottomed flask equipped with magnetic stirbar was charged with 400 mL anhydrous tetrahydrofuran (THF). The flask was stirred and purged with N₂ while 10.56 g lithium aluminum hydride (0.278 mol, 1.75 equiv) was added over 10 min. A reflux condenser was attached to the flask, and an addition funnel with N₂ bubbler was connected on top of the condenser. The funnel was charged with a solution of 41.58 g compound 9 (0.159 mol) in 100 mL anhydrous THF. The ester was added over 20 min. The mixture was then refluxed until thin-layer chromatography (TLC) showed complete consumption of the ester (30 min). The mixture was cooled in an ice bath and carefully quenched with 10.56 mL H₂O followed by 10.56 mL 15% NaOH and finally 31.68 mL H₂O. After stirring 1 h, the mixture was filtered through diatomaceous

Example 4

The preparation of 6-diethylaminobenzo[b]furan-2-carboxaldehyde, compound 11 in Scheme 1. A 2-L round-bottomed flask equipped with magnetic stirbar was charged with 36.53 g 2,3,5,6-tetrachloro-1,4-benzoquinone (0.149 mmol, 1.1 equiv) and 900 mL CHCl₃. An addition funnel was attached, and 2948 g compound 10 (0.135 mol) dissolved in 100 mL CHCl$_3$ were added over 20 min. The mixture heated to 40° C. for 8 h. After this time, TLC showed the alcohol was completely consumed. The dark mixture was cooled to rt, and the precipitated 2,3,5,6-tetrachloro-1,4-hydroquinone[32.44 g (97%), mp 235-238° C. (HOAc), dH (DMSO): 10.21 (bs, 20H); dC (DMSO): 144.11, 120.74] was filtered. The solvent was stripped at the rotovap, and 500 mL 50% hexanes/Et$_2$O were added. The supernatant was decanted away from some dark residues on the flask wall. The solution was then chromatographed on silica gel to give the title compound as a yellow-brown oil (22.56 g, 77%). dH (CDCl$_3$): 9.63 (s, 1H), 7.50 (d, J½9.2, 1H), 7.41 (d, J½1.0, 1H), 6.77 (dd, P/48.9 and 2.3 Hz, 1H), 6.71 (d, J½2.0 Hz, 1H), 3.45 (q, J½7.2 Hz, 4H), 1.23 (t, J½7.1 Hz, 6H); dC (CDCl$_3$): 177.79, 159.92, 151.33, 150.14, 124.18, 116.08, 111.49, 92.73, 45.22, 12.66.

Example 5

The preparation of (E)-3-(2-(6-(diethylamino)benzo[b]furan-2-yl)vinyl)-5,5-dimethylcyclohex-2-enone, compound 12 in Scheme 1. A 250-mL round-bottomed flask equipped with magnetic stirbar and reflux condenser was charged with 8.4 g compound 11 (39 mmol), 5.34 g isophorone (39 mmol, 1 equiv), and 50 mL EtOH. Over 5 min, a solution of 1.55 g NaOH (39 mmol, 1 equiv) in 5 mL H$_2$O was added dropwise. The mixture was heated to reflux for 15 min and then allowed to cool to rt. The mixture was poured into 200 mL H$_2$O and neutralized with 2.2 mL glacial HOAc (39 mmol, 1 equiv). The mixture was extracted three times with 100-mL portions of Et$_2$O. The organic phases were collected and washed once with 100 mL H$_2$O followed by 100 mL brine. The organic phase was dried over anhydrous MgSO$_4$ and rotary evaporated to a crude orange solid. Recrystallization from heptane gave 12.07 g of the title compound as orange needles (93%). Mp 102-104° C. dH (CDCl$_3$): 7.33 (d, J½9.0 Hz, 1H), 6.93 (d, Jab½15.7 Hz, 1H), 6.81 (d, Jab½16.2 Hz, 1H), 6.71 (d, J½1.8 Hz, 1H), 6.66 (dd, J½8.7 and 2.3 Hz, 1H), 6.66 (s, 1H), 6.08 (s, 1H), 3.41 (q, J½7.1 Hz, 4H), 2.42 (s, 2H), 2.29 (s, 2H), 1.20 (t, J½6.9 Hz, 6H), 1.09 (s, 6H); dC (CDCl$_3$): 200.12, 158.26, 154.77, 151.71, 147.76, 127.41, 126.54, 122.59, 121.77, 118.15, 109.99, 109.55, 93.35, 51.55, 45.09, 38.99, 33.41, 28.66, 12.72. Elemental analysis calculated for C$_{22}$H$_{27}$NO$_2$: C, 7823; H, 8.00; N, 4.15. Found: C, 78.21; H, 8.06; N, 4.13.

Example 6

The preparation of (E and Z)-2-(3-((E)-2-(6-(diethylamino)benzo[b]furan-2-yl)vinyl)-5,5-dimethylcyclohex-2-enylidene)acetonitrile, compound 13 in Scheme 1. A 1-L round-bottomed flask equipped with magnetic stirbar and 200-mL addition funnel was charged with 200 mL anhydrous THF and 13.3 g anhydrous MeCN (320 mmol, 9 equiv). The apparatus was protected by N$_2$ bubbler and cooled in a dry ice/acetone bath. The addition funnel was charged with 126 mL of 2.3M hexyllithium in hexanes (290 mmol, 8 equiv), which were added over 30 min. During the addition, the lithioacetonitrile precipitated as a white solid. After 20 min, a new addition funnel was equipped and charged with a previously prepared solution of 12.07 g compound 12 (36 mmol) in 30 mL anhydrous THF. The ketone solution was run in over 20 min. The cooling bath was then removed, and the mixture was stirred at rt overnight. A saturated aqueous solution of NH$_4$Cl (100 mL) and 250 mL Et$_2$O was added, and the mixture was vigorously stirred. The organic layer was separated and washed with 100 mL H$_2$O followed by 100 mL brine. The organic layer was dried over anhydrous MgSO$_4$ and rotary evaporated to an orange oil, which was the intermediate β-hydroxynitrile. The oil was dissolved in 200 mL glacial HOAc in a 500-mL round-bottomed flask and refluxed for 5 h. After this time, the reaction was complete by TLC. The glacial HOAc and other volatiles were rotary evaporated, leaving a crude orange solid. Recrystallization from MeCN gave the title compound as orange needles (7.75 g, 60%). Mp 138-140° C. dH (CDCl$_3$): 7.32 (d, J½8.7 Hz, 1H), 7.03-6.25 (m, 6H), 5.12 (s, 0.54H, trans), 4.95 (s, 0.44H, cis), 3.42 (q, J½7.0 Hz, 4H, cis), 3.41 (q, J½7.0 Hz, 4H, trans), 2.49-2.21 (m, 4H), 1.22 (t, J½7.0 Hz, 3H, cis), 1.21 (t, J½7.0 Hz, 3H, trans), 1.06-0.98 (m, 6H); dC (CDCl$_3$): 158.19, 157.69, 152.46, 152.41, 147.56, 145.01, 144.67, 128.69, 128.36, 126.91, 124.70, 121.55, 121.49, 119.94, 119.77, 118.64, 118.56, 110.00, 107.96, 107.87, 93.83, 93.69, 93.32, 91.89, 45.21, 44.87, 42.28, 39.03, 38.93, 31.42, 31.26, 28.37, 28.32, 12.82. Elemental analysis calculated for C$_{24}$H$_{28}$N$_2$O: C, 79.96; H, 7.83; N, 7.77. Found: C, 79.84; H, 7.91; N, 7.90.

Example 7

The preparation of (E and Z)-2-(3-((E)-2-(6-(Diethylamino)benzo[b]furan-2-yl)vinyl)-5,5-dimethylcyclohex-2-enylidene)acetaldehyde, compound 14 in Scheme 1. A 500-mL round-bottomed flask equipped with a magnetic stirbar was charged with 7.75 g compound 13 (22 mmol) and 250 mL toluene. The mixture was cooled in a dry ice/acetone bath. A 100-mL addition funnel and N$_2$ bubbler were equipped, and the funnel was charged with 32 mL 1M diisobutylaluminum hydride in hexanes (32 mmol, 1.5 equiv), which was added over 1 h. The mixture was stirred at rt for 12 h. After this time, a paste of 30 g SiO$_2$ and 10 mL H$_2$O was added, followed by 1 g oxalic acid dihydrate. The mixture was stirred another 12 h to allow complete hydrolysis of the imine intermediate. The mixture was filtered through celite to remove insolubles. The organic phase was separated and washed with 100 mL H$_2$O followed by 100 mL brine. After drying over anhydrous MgSO$_4$, the solvent was rotary evaporated, leaving an orange oil. The crude product was chromatographed on SiO$_2$ (hexanes/EtOAc) to obtain 6.92 g of the title compound as an orange oil (88%). dH (CDCl$_3$): 10.22 (d, J½8.2 Hz, 0.37 Hz, cis), 10.01 (d, J½8.4 Hz, 0.63H, trans), 7.32 (d, J½8.6 Hz, 1H), 7.02-6.89 (m, 1H), 6.75-6.33 (m, 4H), 5.94 (d, J½8.4 Hz, 0.66H, trans), 5.74 (d, J½8.4 Hz, 0.52H, cis), 3.41 (q, J½7.0 Hz, 4H), 2.71-2.26 (m, 4H), 1.21 (t, J½7.0 Hz, 6H), 1.08-0.99

Example 8

Methods for the preparation of dimethyl-tricyanodihydrofuran (TCF) electron-acceptor end group are well established, for example, see Davis, M. C.; Chafin, A. P.; Hollins, R. A.; Baldwin, L. C.; Erickson, E. D.; Zarras, P.; Drury, E. C. *Synth. Commun.* 2004, 34, 3419-3429. Ethyl vinyl ether is deprotonated with tert-butyllithium at −78° C. and then reacted with acetone to give, after hydrolysis, the intermediate 3-hydroxy-3-methyl-2-butanone. The latter is then reacted with two equivalents of malononitrile in ethanol having a small amount of sodium ethoxide to give the tricyanofuran acceptor.

Example 9

The preparation of a benzofuran dye having a dimethyl-TCF electron-acceptor group, namely, (E and Z)-2-(3-Cyano-4-(3-(3-((E)-2-(6-(diethylamino)benzo[b]furan-2-yl)vinyl)-5,5-dimethylcyclohex-2-enylidene)prop-1-enyl)-5,5-dimethylfuran-2(5H)-ylidene)malononitrile. A 50-mL round-bottomed flask equipped with magnetic stirbar was charged with 1 g compound 14 (2.8 mmol), 547 mg TCF (1 equiv), and 15 mL $CH_2Cl_2$. The mixture was heated briefly to dissolve all the solids. One portion of 400 mg piperidinium acetate (1 equiv) was added, and the mixture was heated to 40° C. for 2 h. During this time, a dark purple solid precipitated. After cooling to rt, the solid was collected on a medium-porosity glass frit. After washing with EtOH, the product was air-dried on the frit (1 g, 67%). The product was recrystallized from MeCN to give the title compound as microscopic purple needles. Mp 243-245° C. kmax¼697 nm. dH ($CDCl_3$): 8.26 (dd, J¼15.1 and 13.7 Hz, 0.15H, cis), 7.99 (dd, J¼15.1 and 12.5 Hz, 0.85H, trans), 7.33 (d, J¼8.6 Hz, 1H), 7.05-6.59 (m, 5H), 6.48-6.09 (m, 3H), 3.43 (q, J¼6.7 Hz, 4H), 2.43 (s, 2H), 2.37 (s, 2H), 1.72-1.67 (m, 6H), 1.22 (t, J¼7.0 Hz, 6H), 1.08-1.03 (m, 6H). Elemental analysis calculated for $C_{33}H_{34}N_4O_2$: C, 76.42; H, 6.61; N, 10.80. Found: C, 76.71; H, 6.66; N, 10.57.

The working Examples 10-15 describe the synthetic steps involved in preparing benzofuran dyes similar to BFFH-10 and BFFH-11 shown in Table 1 (some of which are published in *Optical Materials* 2011, 33, 1307-1315). The dyes described in working Examples 10-15 include bulky side groups that improve solubility and eliminated aggregation, especially when the dye is dissolved in a polymer host material, but also in other embodiments of the invention when the dye is attached to a polymer or other solid matrix construction. The steps for the preparation of a BFFH dye including a bulky side group are outlined in Scheme 2 shown directly below. Compound 16 in Scheme 2 is the BFFH dye that was used in a guest-host NLO material in Examples to follow. A guest-host material is a dye dissolved in a polymer. Compound 4 in Scheme 2 is the same as intermediate compound 11 shown in Scheme 1 and discussed in Example 4.

Scheme 2.

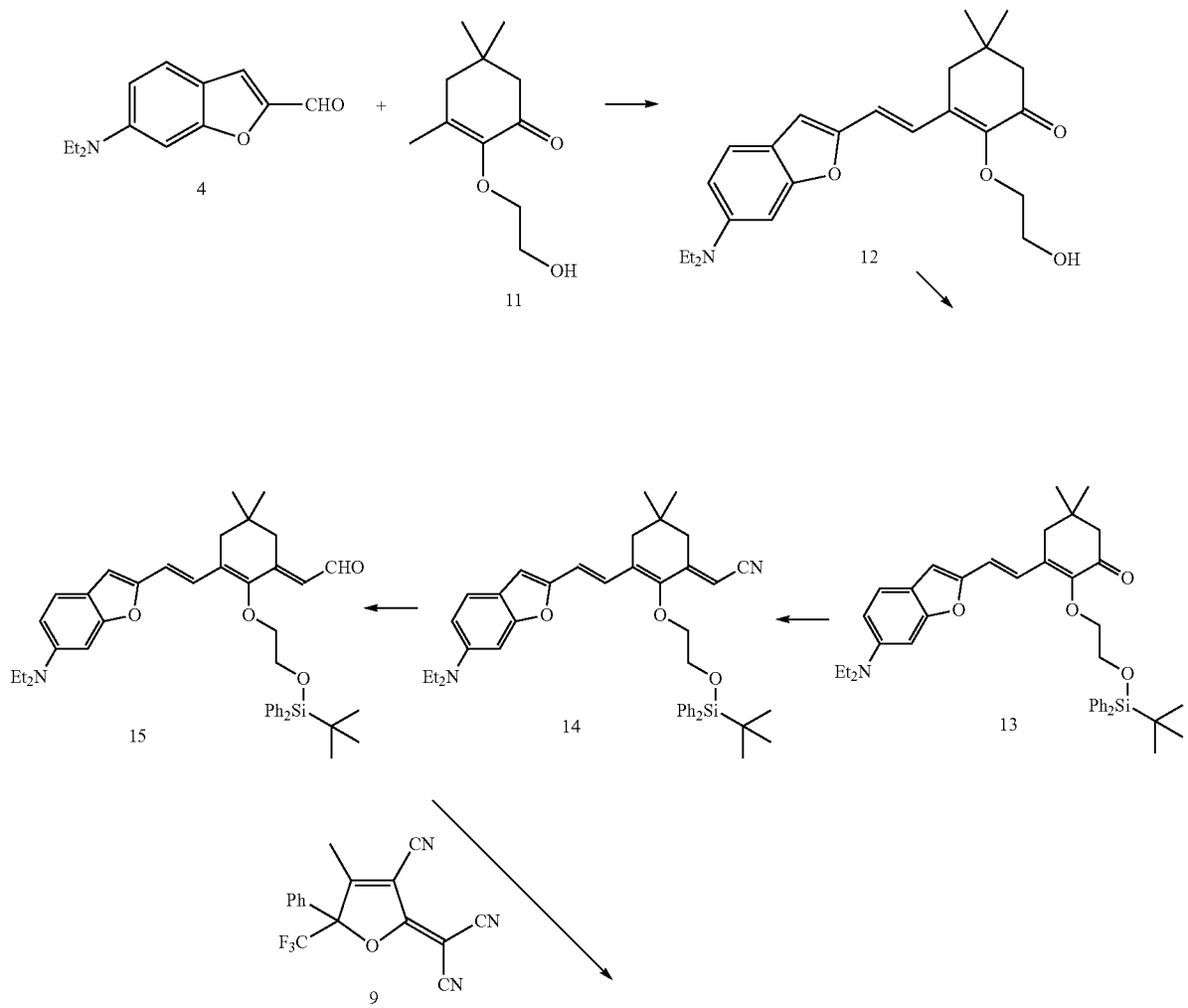

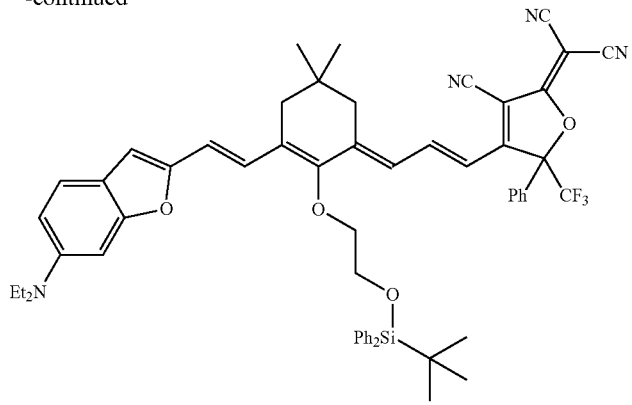

16

Example 10

The preparation of hydroxyethyloxy-isophorone (compound 11 in Scheme 2) was accomplished by reacting isophorone oxide with excess ethylene glycol. 2-(2-Hydroxyethoxy)-3,5,5-trimethylcyclohex-2-enone was prepared as follows: 20.0 g 4,4,6-trimethyl-7-oxabicyclo[4.1.0]heptan-2-one (130 mmol) was added to a solution of 3.0 g sodium (130 mmol) in 150 mL ethylene glycol. The solution was heated to 50° C. and stirred for 18 h then cooled and poured into 500 mL water. This was extracted with 2×250 mL $CH_2Cl_2$. The combined extracts were washed with water then dried ($MgSO_4$) and concentrated in vacuum to give 24.14 g of a tan liquid (94%) This was distilled at 0.13 torr (collected 105° C. to 110° C.) to give 18.35 g of 11, a light yellow liquid (71%). 1H NMR (acetone-d6): 4.0 (t, 1H), 3.79 (t, 2H), 3.59 (m, 2H), 2.31 (s, 2H), 2.2 (s, 2H), 1.88 (s, 3H), 1.00 (s, 6H).

Example 11

The preparation of (E)-3-(2-(6-(Diethylamino)benzofuran-2-yl)vinyl)-2-(2-hydroxy ethoxy)-5,5-dimethylcyclohex-2-enone (compound 12 in Scheme 2) was as follows: 2.3 g sodium (100 mmol) was dissolved in 50 mL MeOH. To this was added a solution of 6.35 g compound 4 (29 mmol) and 5.8 g compound 11, Scheme 2 (29 mmol) in 150 mL MeOH. The solution was heated to 60° C. and stirred overnight. The mixture was poured into 200 mL $CH_2Cl_2$ and washed with water and brine then dried ($MgSO_4$) and concentrated in vacuum to give 10.78 g of a red glassy solid. This was chromatographed on Silica Gel using 50% EtOAc/hexanes to give 9.57 g of a red glass (83%). 1H NMR (Acetone-d6): 7.5 (d, 1H), 7.4 (d, 1H), 6.9 (d, 1H), 6.73 (s, 1H), 6.7 (m, 2H), 3.97 (t, 2H), 3.71 (q, 2H), 3.48 (q, 4H), 2.57 (s, 2H), 2.34 (s, 2H), 1.2 (t, 6H), 1.1 (s, 6H). MS (EI): 397 (M+), 324.

Example 12

The preparation of (E)-3-(2-(6-(diethylamino)benzofuran-2-yl)vinyl)-2-(2-(tertbutyldiphenylsilyloxy)ethoxy)-5,5-dimethylcyclohex-2-enone (compound 13 in Scheme 2) was as follows: To a solution of 12.48 g compound 12, Scheme 2 (31 mmol) and 9.0 g chloro t-butyldiphenylsilane (33 mmol) in 150 mL dimethylformamide was added 2.23 g imidazole (33 mmol). The mixture was stirred for 4 h then poured into 300 mL chloroform. This was washed with 1 N HCl and water then dried ($MgSO_4$) and concentrated in vacuum to give 18.59 g of a reddish solid. This was triturated with ether to give 15.06 g of an orange solid (76%). 8.0 g of this was recrystallized from 200 mL ethanol and 20 mL water to give 6.19 g of orange crystals (59%). 1H NMR (Acetone-d6): 7.7 (m, 4H), 7.6 (d, 1H), 7.35 (m, 6H), 7.3 (d, 1H), 6.9 (d, 1H), 6.75 (s, 1H), 6.6 (m, 1H), 6.5 (s, 1H), 4.12 (t, 2H), 3.94 (t, 2H), 3.38 (q, 4H), 2.57 (s, 2H), 2.31 (s, 2H), 1.1 (m, 21H). MS (EI): 635 (M+), 578.

Example 13

The preparation of (E)-2-(2-(2-(tert-butyldiphenylsilyloxy)ethoxy)-3-((E)-2-(6-(diethylamino)benzofuran-2-yl) vinyl)-5,5-dimethylcyclohex-2-enylidene)acetonitrile (compound 14 in Scheme 2) was as follows: A solution of 5 mL dry $CH_3CN$ (96 mmol) in 100 mL THF was cooled to −70° C. while 35 mL 2.5M n-BuLi (88 mmol) was added dropwise. After 15 min at −70° C. a solution of 7.0 g compound 13, Scheme 2 (11 mmol) in 150 mL THF was added. The mixture was stirred at −70° C. for 10 min then allowed to warm to 0° C. 100 mL water was then added and the mixture was concentrated in vacuum. The residue was taken up in 250 mL $CH_2Cl_2$ and washed with water then dried ($MgSO_4$) and concentrated in vacuum to give 8.71 g of a dark red oily solid. This was taken up in 100 mL HOAc. The solution was heated to 60° C. and stirred overnight. The solution was cooled and poured into 300 mL $CHCl_3$. This was washed well with water then dried ($MgSO_4$) and concentrated in vacuum to give 7.15 g of a red glass. This was chromatographed on Silica Gel using 30% EtOAc/hexanes to give 3.17 g of a red glass (44%). MS (EI): 658 (M+), 635.

Example 14

The preparation of (E)-2-(2-(2-(tert-butyldiphenylsilyloxy)ethoxy)-3-((E)-2-(6-(diethylamino)benzofuran-2-yl) vinyl)-5,5-dimethylcyclohex-2-enylidene)acetaldehyde (compound 15 in Scheme 2) was as follows: A solution of 5.48 g compound 14, Scheme 2 (1.3 mmol) in 60 mL toluene was cooled to −70° C. while 18 mL 1.5M Dibal-H in toluene was added. The solution was stirred for 4 h at −70° C. then about 15 g of wet silica gel was added along with 30 mL ether. The mixture was allowed to warm to room temperature (typically ranging from about 20 to about 23° C.) and stirred overnight. The solids were then filtered off and the filtrate concentrated in vacuum to give 5.55 g of a red glass. This was chromatographed on Silica Gel using 30% EtOAc/hexanes to give 2.69 g of a red glass (52%). 1H NMR (Acetone-d6): 10.1 (d, 1H, CHO).

Example 15

The preparation of the trifluoromethyl(phenyl)-tricyanodihydrofuran ($CF_3$-TCF) electron-acceptor end group. 2-(3-Cyano-4-methyl-5-phenyl-5-(trifluoromethyl)furan-2-(5H)-ylidene)-malononitrile (compound 9), shown in Scheme 2, was prepared as follows: A mixture of 19.23 gms of 4,4,4-trifluoro-3-hydroxy-3-phenylbutan-2-one (88 mmoles), 12.81 gms malononitrile (194 mmoles, 2.2 eq) and 0.2 gins DMAP in 30 mL pyridine was heated to 50° C. and stirred overnight. The mix was cooled and poured into 200 mL $CH_2Cl_2$. This was washed with 100 mL 4 N HCl and brine then dried ($MgSO_4$) and concentrated in vacuum to give 24.19 gms of a dark glass. This was recrystallized from 100 mL toluene to give 7.72 gins of compound 9, a white solid (28%). $^1$H NMR (Acetone-$d_6$): 7.8 (m, 2H), 7.63 (m, 3H), 2.57 (s, 3H).

Example 16

The preparation of 2-(4-((1E,3E)-3-(2-(2-(tert-butyldiphenylsilyloxy)-3-((E)-2-(6-(diethylamino)benzofuran-2-yl)vinyl)-5,5-dimethylcyclohex-2-enylidene)prop-1-enyl)-3-cyano-5-phenyl-5-(trifluoromethyl)furan-2(5H)-ylidene) malononitrile (the BFFH-11-type ethoxysiloxane-benzofuran dye, compound 16 in Scheme 2) was as follows: a solution of 2.69 g compound 15, Scheme 2 (4.3 mmol) and 1.4 g compound 9 (4.3 mmol) in 50 mL ethanol were heated to 65° C. and stir for 5 h then cool and concentrate the solution in vacuum. The residue was chromatographed twice on Silica Gel using 30% EtOAc/hexanes and 20% EtOAc/hexanes to give 0.60 g of a blue solid (15%). MS (ESI): 959 (M+).

The working Examples 17-35 demonstrate the synthetic steps involved in preparing a morpholene-substituted benzofuran dye (similar to the BFFH-11 structure shown in Table 1. Scheme 3 (directly below) shows the chemical structures of the intermediates for each step in the preparation of this dye.

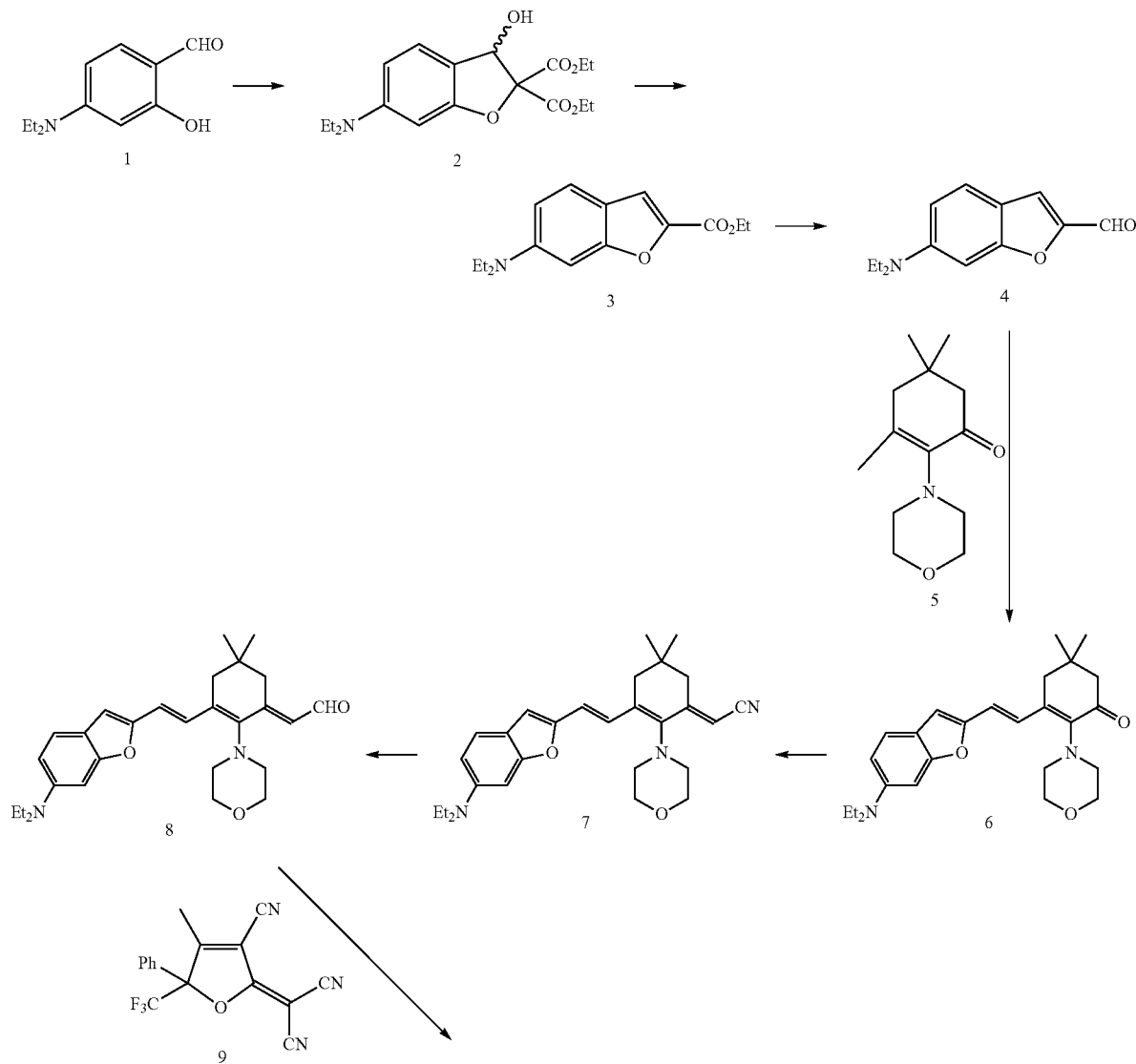

Scheme 3.

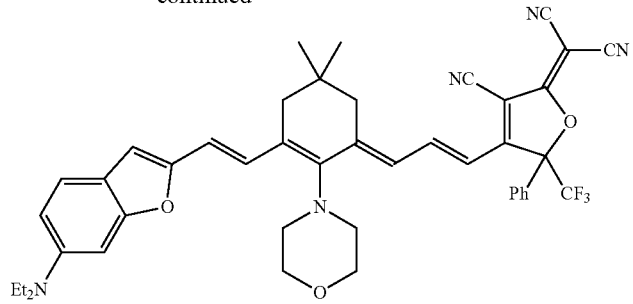

10

Example 17

The preparation of 2-Morpholino-isophorone (compound 5), as shown in Scheme 3. Isophorone (100 g, 0.72 mol), N-bromosuccinimide (128 g, 0.72 mol) and carbon tetrachloride (300 mL) were added to a 1000 mL round bottom flask and fitted with a stirbar and condenser. The mixture was placed under nitrogen and stirred at room temperature for 30 minutes and then refluxed for 30 minutes. The filtrate was collected by vacuum filtration and the solvent was removed under reduced pressure to yield a yellow oil. To this oil was added petroleum ether (250 mL) and refrigerated overnight at 0° C. The resulting crystals of 4-bromo-isophorone were collected by vacuum filtration and dried (121 g, 77%). $^1$H NMR (CDCl$_3$) δ 5.80 (t, 1H, J=1.2 Hz), 4.34, (d, 1H, J=1.5 Hz) 2.59 (d, 1H, J=1.0), 2.53 (d, 1H, J=1.0 Hz), 1.27 (s, 3H), 1.16 (s, 3H); $^{13}$C NMR (CDCl$_3$) δ 198.2, 157.4, 126.0, 61.7, 46.2, 37.5, 29.9, 24.9, 22.6.

Example 18

The preparation of (E)-3-(2-(6-(diethylamino)benzofuran-2-yl)vinyl)-5,5-dimethyl-2-morpholino-cyclohex-2-enone (compound 6), as shown in Scheme 3. 2-Morpholino-isophorone (compound 5) (1.40 g, 6.28 mmol), benzofuran carboxaldehyde (1.50 g, 6.90 mmol) (compound 4), and 0.1M sodium methoxide in methanol (25 mL) were added to a 50 mL round bottom flask which was fitted with a stirbar and reflux condenser. The mixture was placed under nitrogen and refluxed overnight. The precipitate was collected by vacuum filtration, washed with cold methanol and dried (2.40 g, 91%). No further purification of 6 was employed in this embodiment. $^1$H NMR (CDCl$_3$) δ 7.80 (d, 1H, J=16.5 Hz), 7.33 (d, 1H, J=8.7 Hz), 6.74 (d, 1H, J=16.4 Hz), 6.74 (d, 1H, J=2.3 Hz), 6.67 (dd, 1H, J=8.7 Hz, J=2.3 Hz), 6.63 (s, 1H), 3.86 (t, 4H, J=4.7 Hz), 3.44 (q, 4H, J=7.1 Hz), 3.09 (b, 4H), 2.49 (s, 2H), 2.33 (s, 2H), 1.23 (t, 6H, J=7.1 Hz), 1.08 (s, 6H); $^{13}$C NMR (CDCl$_3$) δ 198.0, 158.0, 152.6, 147.5, 145.8, 142.2, 124.4, 121.6, 121.4, 118.2, 109.8, 108.5, 93.5, 68.0, 52.8, 51.2, 44.9, 39.5, 32.3, 28.4, 12.6; IR (KBr) cm$^{-1}$=1649.

Example 19

The preparation of (E)-2-(3-((E)-2-(6-(diethylamino)benzofuran-2-yl)vinyl)-5,5-dimethyl-2-morpholinocyclohex-2-enylidene)acetonitrile (compound 7), as shown in Scheme 3. Diisopropylamine (3.3 mL, 24 mmol) was added to anhydrous THF (40 mL) placed under nitrogen and cooled to −78° C. To this solution was added 2.5 M butyl lithium in hexanes (9.5 mL, 24 mmol) drop wise. This solution was allowed to warm up to 0° C. and maintained at this temperature for 10 minutes. The solution was cooled back to −78° C. and anhydrous acetonitrile (1.5 mL, 26 mmol) was added dropwise. This solution was warmed to 0° C. and held for 10 minutes and cooled back down to −78° C. To this slurry was added the ketone (compound 6) (1.0 g, 2.37 mmol) dropwise in anhydrous THF (10 mL). The slurry was warmed to 0° C. and allowed to stir for 30 minutes. The reaction was quenched with water (50 mL) and extracted with ethyl acetate (3×25 mL). The extractions were combined, washed with water (3×25 mL) and brine (3×25 mL) and dried over magnesium sulfate. The solvent was removed under reduced pressure and was refluxed overnight with glacial acetic acid (25 mL). The mixture was cooled to room temperature and neutralized with sodium carbonate and extracted with ethyl acetate (3×25 mL). The extractions were combined, washed with water (3×25 mL) and brine (3×25 mL). The solvent was removed under reduced pressure and the residue was purified by column chromatography (9:1, hexanes:ethyl acetate) to yield the nitrile, compound 7, as a red solid (0.77 g, 73%). $^1$H NMR (CDCl$_3$) δ 7.28 (d, 1H, J=15.6 Hz), 7.32 (d, 1H, J=8.6 Hz), 6.82 (d, 1H, J=1.8 Hz), 6.66 (dd, 1H, J=8.7 Hz, J=2.3 Hz), 6.60 (s, 1H), 6.58 (d, 1H, J=15.8 Hz), 5.91 (s, 1H), 3.80 (t, 4H, J=4.3 Hz), 3.43 (q, 4H, J=7.1 Hz), 3.12 (b, 4H), 2.51 (s, 2H), 2.35 (s, 2H), 1.23 (t, 6H, J=7.1 Hz), 1.02 (s, 6H); $^{13}$C NMR (CDCl$_3$) δ 157.9, 157.4, 152.5, 147.3, 142.1, 136.4, 123.8, 121.2, 119.5, 119.4, 118.3, 109.7, 107.9, 93.7, 91.9, 68.3, 50.8, 45.0, 42.9, 40.5, 30.1, 28.0, 12.7; IR (KBr) cm$^{-1}$=2202.

Example 20

The preparation of (E)-2-(3-((E)-2-(6-(diethylamino)benzofuran-2-yl)vinyl)-5,5-dimethyl-2-morpholinocyclohex-2-enylidene)acetaldehyde (compound 8), as shown in Scheme 3. The nitrile 7 (0.4 g, 0.9 mmol) was dissolved in toluene (15 mL) and cooled to −78° C. under a blanket of nitrogen. DIBAL (1.5 M, 1.3 mL) was added to this solution and stirred for 2 hours. Ethyl acetate (15 mL) was added to the solution which was then allowed to slowly warm to room temperature. Saturated ammonium chloride solution (25 mL) was added and stirred for 30 minutes. The organic layer was extracted and dried with brine (3×25 mL) and magnesium sulfate. The solvent was removed under reduced pressure and the resulting oil, the extended aldehyde, compound 8 in Scheme 3, was used without further purification.

Example 21

Preparation of the benzofuran dye, compound 10 in Scheme 3, namely 2-(Cyano-4-((1E,3E)-3-(3-((E)-2-(6-(diethylamino)benzofuran-2-yl)vinyl)-5,5-dimethyl-2-morpholinocyclohex-2-enylidene)prop-1-enyl)-5-phenyl-5-(trifluoromethyl)furan-2-(5H)-ylidene)malononitrile. The extended aldehyde 8 (300 mg) and the CF3-TCF acceptor (compound 9, prepared as per Example 14) (350 mg) were added to ethanol (30 mL) which was refluxed under nitrogen. The progress of the reaction was monitored with TLC and no trace of starting material was observed after 2 hours. The solution was cooled and the ethanol solvent was removed by evaporation under reduced pressure to concentrate the solution. A precipitate formed which was filtered under vacuum and dried under nitrogen to give a dark powder (290 mg, 58%). 1H NMR (CDCl$_3$) δ 7.95 (dd, 1H, J=12.9 Hz, J=12.8 Hz), 7.53 (m, 5H), 7.47 (d, 1H, J=16.3 Hz), 7.32 (d, 1H, J=8.7 Hz), 6.98 (d, 1H, J=12.6 Hz), 6.76 (s, 1H), 6.68 (d, 1H, J=15.6 Hz), 6.66 (s, 1H), 6.46 (d, 1H, J=14.7 Hz), 3.86 (t, 4H, J=4.4 Hz), 3.45 (q, 4H, J=7.0 Hz), 3.12 (b, 4H), 2.43 (m, 2H), 2.23 (m, 2H), 1.24 (t, 6H, J=7.0 Hz), 0.98 (s, 3H), 0.90 (s, 3H).

The working Examples 22-40 demonstrate the synthetic steps involved in preparing two different benzimidazole dyes (similar to the BFFH-8 and -16 dyes shown in Table 1). Scheme 4 (directly below) shows the chemical structures involved in the first six steps used for the preparation of the electron-donor end of one type of benzimidazole dye. In this case a bulky isobutyl group is attached to the BFFH ring. Working Examples 22-27 describe the details of the synthetic steps outlined in Scheme 4.

phases were separated. The organic layer was washed with 100 mL H$_2$O followed by 100 mL brine. After drying over anhydrous MgSO$_4$ the volatiles were rotary evaporated leaving the crude product as an orange oil. Reduced pressure distillation (1 torr) gave 76.13 g of the title compound in analytically pure form (94%). δ$_H$ (CDCl$_3$): 8.28 (bs, NH), 8.20 (dd, J=9.4 and 6.1 Hz, 1H), 6.47 (dd, J=11.6 and 2.5 Hz, 1H), 6.34 (m, 1H), 3.08 (dd, J=7.0 and 5.3 Hz, 2H), 2.02 (hept, J=6.7 Hz, 1H), 1.06 (d, J=6.7 Hz, 6H); δ$_C$ (CDCl$_3$): 169.49, 166.09, 147.94 (d, J$_{CF}$=13.3 Hz), 130.19 (d, J$_{CF}$=12.5 Hz), 128.99, 130.93 (d, J$_{CF}$=25.1 Hz), 99.46 (d, J$_{CF}$=27.0 Hz), 51.11, 28.02, 20.51; δ$_F$ (CDCl$_3$): -100.1. Elemental analysis calculated for C$_{10}$H$_{13}$FN$_2$O$_2$: C, 56.60; H, 6.17; N, 13.20. Found: C, 56.79; H, 6.19; N, 13.29.

Example 23

The preparation of compound 2 in Scheme 4, namely, N-iso-Butyl-2-nitro-5-(di-n-butylamino)aniline. A 1 L round-bottomed flask equipped with magnetic stirbar and reflux condenser was charged with 70.5 g compound 1, Scheme 4 (333 mmol), 128.7 g dibutylamine (0.99 mmol, 3 equiv), 45 g anhydrous K$_2$CO$_3$ and 100 mL DMAC. The mixture was refluxed for 18 h when the reaction was complete by $^1$H NMR. Water (100 mL) was added and while stirring the

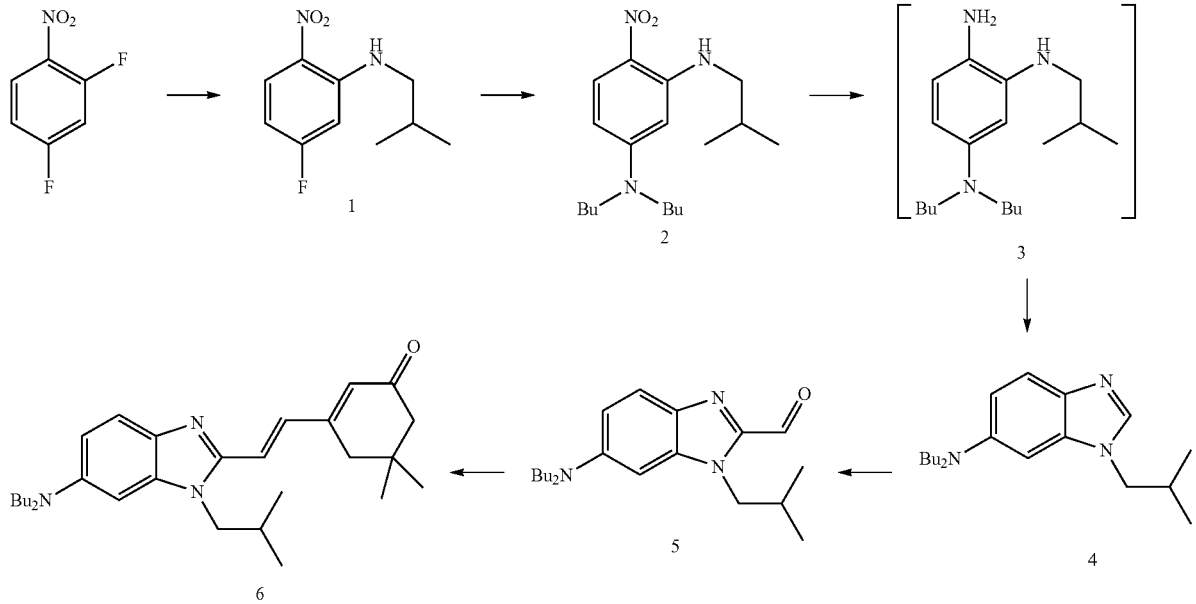

Scheme 4.

Example 22

The preparation of compound 1 in Scheme 4, namely, N-iso-Butyl-2-nitro-5-fluoroaniline. A 500 mL round-bottomed flask equipped with magnetic stirring bar and thermometer was charged with 57.85 g 2,4-difluoronitrobenzene (0.36 mol), 40.44 g TEA (0.4 mol, 1.1 equiv) and 40 mL H$_2$O. The mixture was stirred at in an ice bath while 29.3 g isobutylamine and (39.6 mL, 0.4 mol, 1.1 equiv) was added over 2 h keeping the internal temperature below 50° C. After stirring at rt for 2 h, the reaction was complete by thin-layer chromatography (TLC). Ether (200 mL) was added and the product spontaneously crystallized from the upper layer of dibutylamine. The mixture was filtered through a coarse porosity glass frit to give 95.6 g of the title compound as a bright yellow, microcrystalline powder (89%). The solid could be further purified by recrystallization from hexanes. Mp 60-62° C. δ$_H$ (CDCl$_3$): 8.59 (t, J=4.7 Hz, NH), 8.04 (d, J=9.8 Hz, 1H), 6.04 (dd, J=9.5 and 2.6 Hz, 1H), 5.61 (d, J=2.9 Hz, 1H), 3.33 (dd, J=9.9 and 6.7 Hz, 4H), 3.05 (dd, J=6.8 and 5.4 Hz, 2H), 2.03 (hept, J=6.9 Hz, 1H), 1.61 (pent, J=7.2 Hz, 4H), 1.38 (hex, J=7.8 Hz, 4H), 1.04 (d, J=6.8 Hz, 6H), 0.98 (t, J=7.3 Hz, 6H); δ$_C$ (CDCl$_3$): 153.82, 148.35, 129.46, 123.14, 103.14, 90.49, 51.22, 50.89, 29.79, 27.98, 20.71, 20.47, 14.07. Elemental analysis calculated for $C_{18}H_{31}N_3O_2$: C, 67.25; H, 9.72; N, 13.07. Found: C, 67.42; H, 9.71; N, 13.07.

Example 24

The preparation of compound 3 in Scheme 4, namely, 2-iso-butylamino-4-(di-n-butylamino)aniline. A mixture of 52.25 g compound 2, Scheme 4 (40 mmol), 2 g 5% Pd/C and 700 mL EtOH containing 3 mL HOAc was hydrogenated (50 psi) on a Parr® apparatus for 5 h. The reaction mixture was taken off the hydrogenation apparatus and protected with an atmosphere of nitrogen (note: the product develops a purple color when exposed to air). After filtering through diatomaceous earth to remove the catalyst, the mixture was rotary evaporated leaving 47 g of the crude product as a brown-colored oil (99%). No further purification was performed before use in the next step. The molecule was too oxidatively sensitive to give accurate combustion analyses. $\delta_H$ (DMSO): 6.43 (d, J=8.1 Hz, 1H), 5.90 (d, J=2.6 Hz, 1H), 5.85 (dd, J=8.4 and 2.7 Hz, 1H), 4.37 (t, J=5.5 Hz, NH), 3.85 (bs, $NH_2$), 3.05 (t, J=7.5 Hz, 4H), 2.83 (t, J=6.0 Hz, 2H), 1.88 (hept, J=6.8 Hz, 1H), 1.43 (m, 4H), 1.30 (m, 4H), 0.95 (d, J=6.6 Hz, 6H), 0.89 (t, J=−7.2 Hz, 6H); $\delta_C$ (DMSO): 142.21, 137.89, 125.73, 116.15, 102.87, 98.58, 51.54, 51.38, 29.29, 27.19, 20.45, 19.82, 13.80.

Example 25

The preparation of compound 4 in Scheme 4, namely, 6-(Di-n-butylamino)-1-iso-butyl-1H-benzimidazole. A 250 mL round-bottomed flask equipped with magnetic stirbar and $N_2$ bubbler was charged with 47 g compound 3, Scheme 4 (39 mmol), 179 mL DMAC, 25.6 g trimethyl orthoformate (59 mmol, 1.5 equiv) and 700 mg of p-toluenesulfonic acid monohydrate (1 mmol, 2.5 mol %). The mixture was heated to 80° C. for 1 h. After this time, the reaction was complete by NMR. The mixture was partitioned between 500 mL $Et_2O$ and 500 mL $H_2O$. The organic layer was separated and washed with 300 mL saturated aqueous $NaHCO_3$ and finally 500 mL brine. After drying the organic layer over anhydrous $MgSO_4$, the solvent was rotary evaporated leaving a brown oil. The crude product was distilled at reduced pressure (0.1 torr) to give 47.76 g of the title compound as a pale yellow oil having the viscosity of honey (97%). $\delta_H$ ($CDCl_3$): 7.65 (s, 1H), 7.60 (d, J=8.7 Hz, 1H), 6.76 (dd, J=9.0 and 2.2 Hz, 1H), 6.49 (d, J=2.3 Hz, 1H), 3.86 (d, J=7.1 Hz, 2H), 3.31 (t, J=7.6 Hz, 4H), 2.21 (kept, J=7.1 Hz, 1H), 1.60 (pent, J=7.1 Hz, 4H), 1.38 (hex, J=7.6 Hz, 4H), 1.00-0.93 (m, 12H); $\delta_C$ ($CDCl_3$): 145.92, 141.59, 135.85, 135.72, 120.55, 110.55, 92.57, 52.49, 51.99, 29.60, 29.15, 20.59, 20.41, 14.16. Elemental analysis calculated for $C_{19}H_{31}N_3$: C, 75.70; H, 10.36; N, 13.94. Found: C, 75.45; H, 10.46; N, 14.03.

Example 26

The preparation of compound 5 in Scheme 4, namely, 6-(di-n-butylamino)-1-iso-butyl-1H-benzimidazole-2-carboxaldehyde. A 250 mL round-bottomed flask equipped with magnetic stirring bar, 25 mL addition funnel and $N_2$ bubbler was charge with 2.86 g (9.5 mmol) compound 4, Scheme 4, and 50 mL anhydrous THF. The mixture was stirred in a dry ice/acetone bath. The addition funnel was charged with 7.6 mL 2.5 M butyllithium in hexanes (19 mmol, 2 equiv) which was added dropwise in 10 min. After the addition, the mixture was allowed to warm to −20° C. and held at this temperature for 30 min. The mixture was then cooled back down with the dry ice/acetone bath before 2.08 g anhydrous DMF (28.5 mmol, 3 equiv) was added dropwise over 10 min. After stirring for 30 min, the cooling bath was removed and the mixture was allowed to warm to rt over 2 h. Water (100 mL) was added along with 30 mL saturated aqueous $NH_4Cl$. After stirring for 30 min, the mixture was extracted with three 50 mL portions of $Et_2O$. The organic phases were collected and washed with 25 mL $H_2O$ followed by 25 mL brine. The organic phase was dried over anhydrous $MgSO_4$ and rotary evaporated to yield 2.9 g of an orange oil (95%) that slowly crystallized to a low melting, yellow solid. This yellow solid was used in the subsequent step in this embodiment. $\delta_H$ ($CDCl_3$): 9.92 (s, 1H), 7.69 (d, J=9.2 Hz, 1H), 6.87 (dd, J=9.2 and 2.3 Hz, 1H), 6.31 (d, J=2.3 Hz, 1H), 4.32 (d, J=7.2 Hz, 2H), 3.37 (t, J=7.7 Hz, 4H), 2.23 (hept, J=7.2 Hz, 1H), 1.63 (pent, J=7.2 Hz, 4H), 1.40 (hext, J=7.7 Hz, 4H), 0.99 (t, J=7.2 Hz, 6H), 0.95 (d, J=6.7 Hz, 6H); $\delta_C$ ($CDCl_3$): 183.41, 148.35, 145.48, 139.48, 135.66, 123.04, 113.35, 89.76, 51.68, 51.66, 29.76, 29.59, 20.57, 20.35, 14.17. Elemental analysis calculated for $C_{20}H_{31}N_3O$: C, 72.91; H, 9.48; N, 12.75. Found: C, 72.78; H, 9.52; N, 12.68.

Example 27

The preparation of compound 6 in Scheme 4, namely, (E)-3-(2-(6-(Di-n-butylamino)-1-iso-butyl-1H-benzimidazole-2-yl)vinyl)-5,5-dimethylcyclohex-2-enone hydrate. A 50 mL round-bottomed flask equipped with a magnetic stirring bar was charged with 3.0 g compound 5, Scheme 4, (9.1 mmol), 1.38 g isophorone (10 mmol, 1.1 equiv) and 20 mL EtOH. In one portion, a solution of 200 mg NaOH (5 mmol) in 0.5 mL $H_2O$ was added and the mixture was heated to reflux for 25 min. After this time, the reaction was complete by TLC. Water (20 mL) was added causing a red precipitate to form. The mixture was filtered on a medium porosity glass frit to give the title compound in crude form as a red powder. Recrystallization from heptane gave 2.8 g of the title compound as red needles (70%). This red solid was used in another step in this embodiment. Mp 114-116° C. $\delta_H$ ($CDCl_3$): 7.63 (d, J=15.4 Hz, 1H), 7.58 (d, J=9.2 Hz, 1H), 6.88 (d, J=15.4 Hz, 1H), 6.78 (dd, J=8.7 and 1.9 Hz, 1H), 6.37 (d, J=1.4 Hz, 1H), 6.22 (s, 1H), 3.95 (d, J=6.8 Hz, 2H), 3.34 (t, J=7.7 Hz, 4H), 2.46 (s, 2H), 2.34 (s, 2H), 2.21 (hept, J=7.2 Hz, 1H), 1.62 (pent, J=7.7 Hz, 4H), 1.40 (hex, J=7.7 Hz, 4H), 1.14 (s, 6H), 1.06-0.92 (m, 12H); $\delta_C$ ($CDCl_3$): 200.19, 153.76, 147.59, 146.34, 137.81, 135.63, 134.42, 128.34, 120.46, 119.61, 111.72, 91.34, 51.85, 51.68, 50.94, 39.44, 33.62, 29.92, 29.68, 28.74, 20.69, 20.62, 14.21. Elemental analysis calculated for $C_{29}H_{43}N_3O \cdot 0.75H_2O$: C, 75.13; H, 9.60; N, 9.07. Found: C, 75.02; H, 9.81; N, 8.90.

Additional steps for the preparation of a benzimidazole dye of this embodiment are outlined in Scheme 5 shown directly below. Working Examples 28 and 29 describe the synthetic steps outlined in Scheme 5 to form a BFFH dye that is similar to BFFH-8 shown in Table 1. Compound 9 was the intermediate used in the successful route. Working Examples 30 and 31 demonstrate the preparation of compounds 7 and 8 outlined in Scheme 5, which were intermediates in a route that proved to be unsuccessful for making the dye in this embodiment.

Scheme 5.

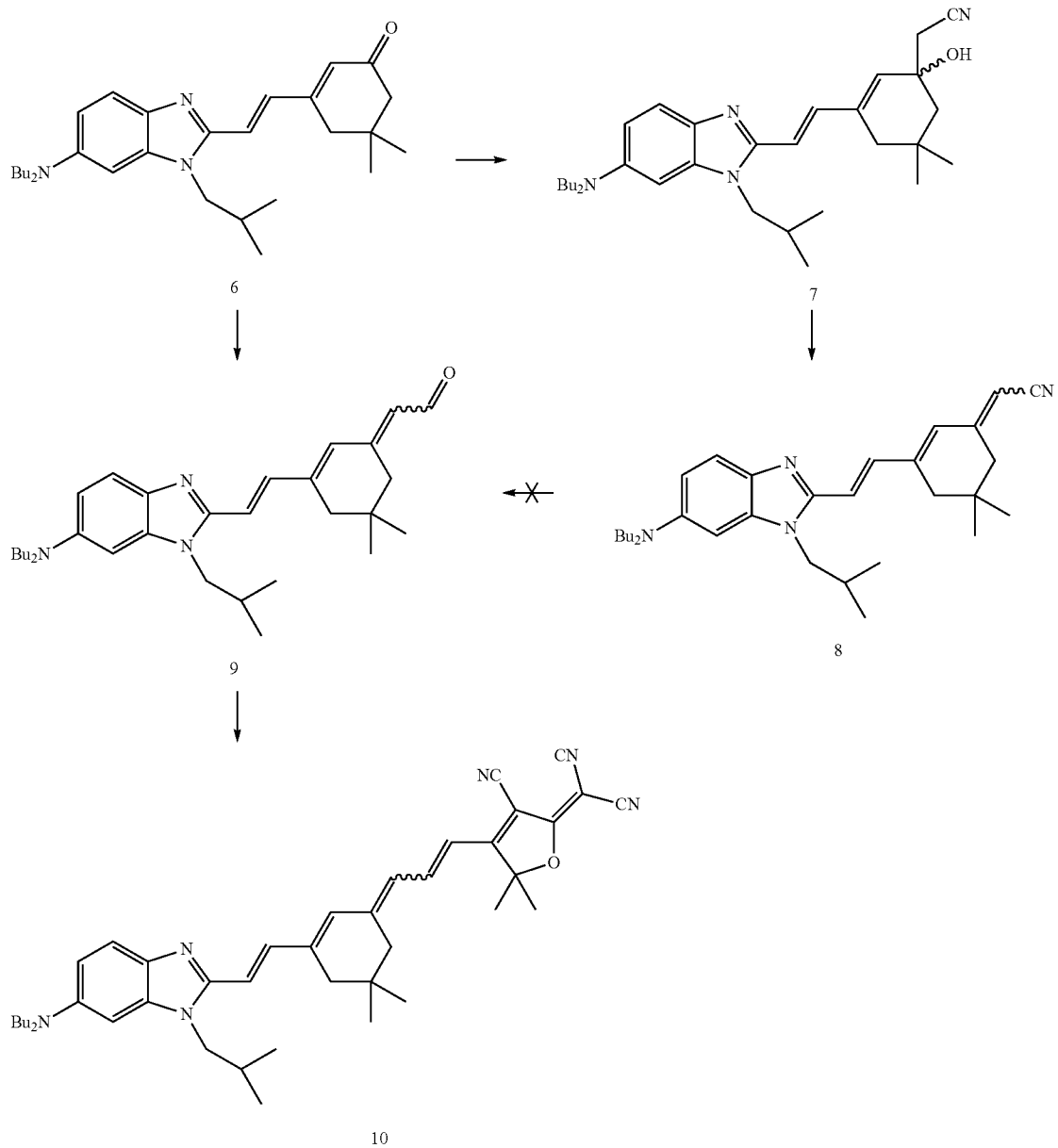

Example 28

The preparation of compound 9 in Scheme 5, namely, (EandZ)-3-(2-(6-(Di-n-butylamino)-1-iso-butyl-1H-benzimidazole-2-yl)vinyl)-5,5-dimethylcyclohex-2-enylidene) acetaldehyde. A 500 mL round-bottomed flask equipped with magnetic stirring bar was charged with 100 mL $Et_2O$ and 1.88 g diisopropylamine (19 mmol, 2.1 equiv). The mixture was cooled in an ice bath and 8.09 mL 2.3 M hexyllithium (19 mmol, 2.1 equiv) in hexanes was added by syringe. After stirring 10 min, the mixture was cooled to −78° C. and 2.32 g N-cyclohexylacetimine (19 mmol, 2.1 equiv) was added dropwise over 15 min. After stirring for 1 h, a solution of 3.97 g compound 6, Scheme 5, (9 mmol) in 20 mL anhydrous THF was added over 20 min. After the addition, the cooling bath was removed and the mixture was stirred at rt for 3 h. The mixture was cooled in an ice bath and 2.32 g HOAc was added dropwise in 5 min followed by a solution of 2.34 g oxalic acid dihydrate in 100 mL $H_2O$. The mixture was stirred at rt overnight. The organic phase was separated and washed with 100 mL $H_2O$ followed by 100 mL brine. After drying over anhydrous $MgSO_4$, the solvent was rotary evaporated leaving a red oil. Silica gel chromatography (25% EtOAc in hexanes) gave 2.44 g of the title compound as a dark red materials, half solid and half oil. This material was triturated with hexanes to give the product as a brick-red powder (58%) which is a 70:30 mixture of E:Z geometric isomers based on NMR. Mp 104-106° C. $\delta_H$($CDCl_3$): 10.22 (d, J=8.3 Hz, 1H, trans), 10.08 (d, J=8.3 Hz, 1H, cis), 7.66 (d, J=15.3 Hz, 1H, trans), 7.62 (d, J=15.6 Hz, 1H, cis), 7.57 (d, J=8.9 Hz, 1H), 7.38 (s, 1H), 6.78 (dd, J=9.2 and 2.2 Hz, 1H), 6.68 (d, J=15.6 Hz, 1H, trans), 6.66 (d, J=15.6 Hz, 1H, cis), 6.47 (s, 1H, cis), 6.38 (s, 1H, trans), 5.97 (d, J=8.4 Hz, 1H, cis), 5.77 (d, J=8.4 Hz, 1H, trans), 3.93 (d, J=7.2 Hz, 2H), 3.33 (t, J=8.1 Hz, 4H), 2.69 (s, 1H), 2.31 (mult, 3H), 2.21 (hex, J=5.9 Hz, 1H), 1.62 (pent, J=6.8 Hz, 4H), 1.39 (hex, J=7.5 Hz, 4H), 1.08 (s, 6H, cis), 1.06 (s, 6H, trans), 1.00 (d, J=6.5 Hz, 6H), 0.98 (t, J=7.3 Hz, 6H); $\delta_C$ (CDCl$_3$): 190.84, 189.70, 155.65, 155.48, 148.32, 146.02, 144.49, 144.35, 137.61, 136.23, 135.29, 132.52, 128.19, 126.40, 124.97, 120.28, 120.03, 116.29, 116.08, 111.47, 91.48, 51.88, 50.87, 46.17, 39.37, 39.12, 38.96, 31.39, 31.28, 29.84, 29.60, 28.59, 28.46, 20.69, 20.60, 14.22. Elemental analysis calculated for C$_{31}$H$_{45}$N$_3$O: C, 78.27; H, 9.53; N, 8.83. Found: C, 78.50; H, 9.79; N, 8.69.

Example 29

The preparation of compound 10 (the finished dye) in Scheme 5, namely, 2-(3-Cyano-4-(3-(3-((E)-2-(6-(di-n-butylamino)-1-iso-butyl-1H-benzimidazole-2-yl))vinyl)-5,5-dimethylcyclohex-2-enylidene)prop-1-enyl)-5,5-dimethyl-furan-2(5H)-ylidene)malononitrile. A 250 mL round-bottomed flask equipped with magnetic stirring bar was charged with 4.14 g compound 12 (8.7 mmol), 1.3 g TCF acceptor (6.5 mmol, 0.75 equiv) and 50 mL CH$_2$Cl$_2$. After all the solids dissolved, 940 mg piperidinium acetate (6.5 mmol, 0.75 equiv) was added in one portion. The mixture quickly became dark green and viscous and was stirred at rt for 1 h. The solvent was rotary evaporated leaving a crude black oil. This oil was suspended in 40 mL EtOH whereupon the product precipitated. The mixture was filtered on a medium-porosity glass frit and the filter cake washed twice with 10 mL portions of EtOH. After air-drying on the flit, 2.3 g of the title compound (54%) was obtained analytically pure as a dark purple powder. $\lambda_{max}$=672 nm (toluene). $\delta_H$ (CDCl$_3$): 7.98 (dd, J=15.0 and 12.0 Hz, 1H), 7.71 (bs, 1H), 7.52 (d, J=9.5 Hz, 1H), 6.72 (d, J=8.7 Hz, 1H), 6.58 (d, J=15.0 Hz, 1H), 6.52 (s, 1H), 6.36 (d, J=12.6 Hz, 1H), 6.28 (s, 1H), 6.22 (d, J=15.0 Hz, 1H), 3.89 (d, J=7.7 Hz, 2H), 3.29 (t, J=7.7 Hz, 4H), 2.38 (s, 2H), 2.30 (s, 2H), 2.14 (pent, J=6.4 Hz, 1H), 1.62 (s, 6H), 1.55 (m, 4H), 1.32 (hext, J=7.7 Hz, 4H), 1.01 (s, 6H), 0.94 (d, J=6.6 Hz, 6H), 0.91 (t, J=7.3 Hz, 6H); $\delta_C$ (CDCl$_3$): 176.10, 173.29, 153.33, 148.39, 146.24, 145.56, 143.54, 137.95, 135.83, 135.40, 133.56, 129.79, 120.21, 117.10, 116.94, 112.47, 111.85, 111.67, 111.62, 97.24, 95.59, 91.18, 56.19, 51.82, 50.87, 39.89, 39.29, 31.59, 29.89, 29.68, 28.69, 26.51, 20.73, 20.70, 20.63, 14.23. Elemental analysis calculated for C$_{42}$H$_{52}$N$_6$O: C, 76.79; H, 7.98; N, 12.79. Found: C, 76.58; H, 8.00; N, 12.57.

Working Examples 30 and 31 are instructive in what did not work as intermediates toward making the final dye in Scheme 5.

Example 30

The preparation of compound 7 in Scheme 5, namely, 3'-(2-(6-(Di-n-butylamino)-1-iso-butyl-1H-benzimidazole-2-yl)vinyl)-5',5'-dimethylcyclohex-2'-ene-1'-hydroxyacetonitrile. A 500 mL round-bottomed flask equipped with magnetic stirring bar, addition funnel and N$_2$ bubbler was charged with 4.43 g anhydrous MeCN (108 mmol, 5 equiv) and 40 mL anhydrous THF. The solution was cooled in a dry ice acetone bath. The addition funnel was charged with 37.8 mL 2.3 M hexyllithium in hexanes (87 mmol, 4 equiv), which was then added dropwise over 30 min. A precipitate forms during this time. A clean addition funnel was attached containing a solution of 9.74 g compound 6, Scheme 5, (22 mmol) in 20 mL anhydrous THF was attached, which was added dropwise over 15 min. The reaction mixture was stirred another 30 min in the cooling bath. Then, 10 mL saturated aqueous NH$_4$Cl was added dropwise and the cooling bath was removed. After stirring at rt for 2 h, the reaction mixture was diluted with 250 mL H$_2$O and extracted with EtOAc (3×100 mL). The organic extracts were collected and washed again with 250 mL H$_2$O followed by 250 mL brine. After drying over anhydrous MgSO$_4$ the solvent was rotary evaporated leaving a yellow-orange solid. Recrystallization from heptane gave the title compound as pale yellow leaflets (9 g, 85%). Mp 125-127° C. $\delta_H$ (CDCl$_3$): 7.50 (d, J=8.2 Hz, 1H), 7.47 (d, J=15.6 Hz, 1H), 6.69 (d, J=8.9 Hz, 1H), 6.45 (d, J=15.6 Hz, 1H), 6.32 (bs, 1H), 5.92 (s, 1H), 3.83 (d, J=7.4 Hz, 2H), 3.60 (bs, 10H), 3.24 (t, J=7.4 Hz, 4H), 2.5 (d, J=16.3, 1H), 2.4 (d, J=16.3 Hz, 1H), 2.20-1.91 (m, 3H), 1.89 (d, J=13.7 Hz, 1H), 1.66 (d, J=13.7 Hz, 1H), 1.52 (m, 4H), 1.38-1.20 (m, 4H), 1.04 (d, J=7.2 Hz, 6H), 0.96-0.75 (m, 12H); $\delta_C$ (CDCl$_3$): 148.47, 145.87, 137.93, 137.82, 137.12, 134.10, 132.54, 119.49, 117.45, 113.85, 111.58, 92.13, 69.57, 63.18, 52.06, 50.94, 47.83, 38.48, 33.09, 32.99, 32.11, 31.84, 31.77, 31.28, 30.54, 30.22, 29.88, 29.84, 29.76, 29.57, 29.54, 27.73, 25.63, 22.87, 22.83, 22.81, 20.64, 20.58, 14.27, 14.17. Elemental analysis calculated for C$_{31}$H$_{46}$N$_4$O: C, 75.87; H, 9.45; N, 11.42. Found: C, 75.87; H, 9.25; N, 11.65.

Example 31

The preparation of compound 8 in Scheme 5, namely, (EandZ)-3-(2-(6-(Di-n-butylamino)-1-iso-butyl-1H-benzimidazole-2-yl)vinyl)-5,5-dimethylcyclohex-2-enylidene) acetonitrile. A 250 mL round-bottomed flask equipped with magnetic stirring bar and reflux condenser was charged with 9 g compound 7, Scheme 5, (18 mmol) and 75 mL glacial HOAc. The mixture was refluxed for 2 h whereby the reaction was complete by TLC. Rotary evaporation of the HOAc gave the crude product as a red oil. Recrystallization from hexanes gave the title compound as garnet colored crystals (7.6 g, 90%). Mp 114-116° C. $\delta_H$ (CDCl$_3$): 7.59 (d, J=15.5 Hz, 1H), 7.52 (d, J=9.1 Hz, 1H), 6.84 (s, 1H), 6.71 (d, J=8.4 Hz, 1H), 6.60 (d, J=15.5 Hz, 1H), 6.32 (bs, 1H), 4.95 (s, 1H), 3.86 (d, J=7.8 Hz, 2H), 3.26 (t, J=7.8 Hz, 4H), 2.29-2.03 (m, 5H), 1.54 (pent, J=6.5 Hz, 4H), 1.31 (hext, J=7.1 Hz, 4H), 0.99-0.85 (m, 18H); $\delta_C$ (CDCl$_3$): 157.10, 148.32, 146.12, 144.07, 137.55, 135.99, 126.93, 120.13, 117.15, 116.52, 111.63, 93.64, 91.58, 51.98, 50.93, 44.72, 39.15, 31.42, 29.85, 29.56, 28.29, 20.66, 20.58, 14.16. Elemental analysis calculated for C$_{31}$H$_{44}$N$_4$: C, 78.77; H, 9.38; N, 11.85. Found: C, 78.59; H, 9.20; N, 11.79.

Examples 32-40 describe the preparations of the precursor compounds and a benzimidazole dye that includes a bulky n-butyl side group and a functional hydroxyethyl group on the amine donor. Structures and reaction schemes leading to the precursor compounds are shown directly before the narrative of each example.

Scheme 6.

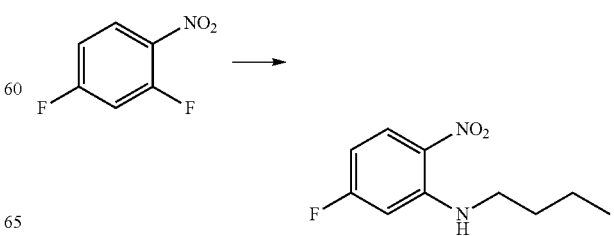

Example 32

The preparation of N-Butyl-5-fluoro-2-nitroaniline shown in Scheme 6. A mixture of 100 grams 2,4-difluoronitrobenzene (0.629 moles) and 96 mL triethylamine (0.689 moles, 1.1 eq) in 80 mL water was cooled in an ice bath while 68 mL n-butylamine (0.689 moles, 1.1 eq) was added dropwise. The mixture was allowed to warm to room temperature and stirred for four hours. 300 mL ether was added and the layers were separated. The organic layer was washed with water, 1N HCl and brine then dried (MgSO$_4$) and concentrated in vacuum to give 126.46 grams of a yellow solid (95%).

Scheme 7.

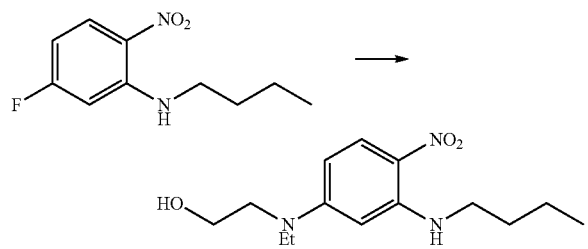

Example 33

The preparation of 2-((3-n-butylamino)-4-nitrophenyl)(ethyl)amino)ethanol, shown in Scheme 7. A mixture of 126.46 grams N-butyl-5-fluoro-2-nitroaniline (0.596 moles), 82.23 grams potassium carbonate (0.596 moles) and 116 mL 2-ethylaminoethanol (1.2 moles, 2 eq) in 500 mL dimethylacetamide was heated to 100° C. under nitrogen and stirred overnight. The solution was cooled and poured into 1 L water. This was extracted with 2×250 mL chloroform. The combined extracts were washed well with water and 1N HCl then dried (MgSO$_4$) and concentrated in vacuum to give 200.1 grams of an orange oil. This was recrystallized from 300 mL toluene to give 118.1 grams of an orange solid (70%).

Scheme 8.

Example 34

The preparation of 2-(-4-amino-(3-n-butylamino)phenyl)(ethyl)amino)ethanol as shown in Scheme 8. A mixture of 40.00 grams 2-((3-n-butylamino)-4-nitrophenyl)(ethyl)amino)ethanol (0.142 moles), 1.5 grams 5% Pd/C and 2 mL glacial acetic acid in 200 mL ethanol was hydrogenated at 50 psi. The mixture was then filtered through Cellite and concentrated in vacuum to give 38.42 grams of a dark brown oil.

Scheme 9.

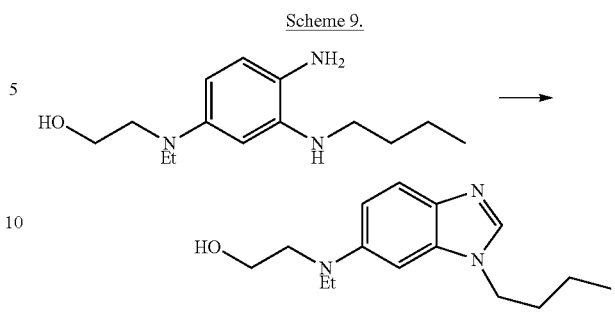

Example 35

The preparation of 2-((1-butyl-1H-benzo[d]imidazol-6-yl)(ethylamino)ethanol as shown in Scheme 9. A mixture of 78.43 grams 2-((4-amino-3-(butylamino)phenyl)(ethyl)amino)ethanol (0.312 moles) and 51 mL methylorthoformate (0.466 moles, 1.5 eq) with 2.0 grams TsOH in 250 mL dimethylacetamide was heated to 100° C. and stirred for four hours. The mixture was cooled and poured into 1 L water. This was extracted with 3×250 mL CHCl$_3$. The combined extracts were washed well with water then dried (MgSO$_4$) and concentrated in vacuum to give 91.16 grams of a black liquid. This was chromatographed in two portions on Silica Gel using 5% MeOH/Acetone to give 72.17 grams of a brown liquid which solidifies on standing (89%). $^1$H NMR (Acetone-d$_6$): 7.68 (s, 1H), 7.33 (d, 1H), 6.67 (d, 2H), 4.1 (t, 2H), 3.7 (t, 2H), 3.4 (m, 4H), 1.75 (q, 2H), 1.3 (q, 2H), 1.1 (t, 3H), 0.85 (t, 3H).

Scheme 10.

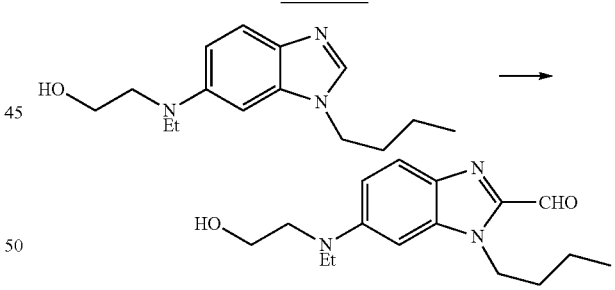

Example 36

The preparation of 2-((1-butyl-1H-2-formyl-benzo[d]imidazol-6-yl)(ethylamino))ethanol, shown in Scheme 10. A solution of 37.87 grams 2-((1-butyl-1H-benzo[d]imidazol-6-yl)(ethylamino))ethanol (0.145 moles) in 500 mL anh. THF under N$_2$ was cooled to −70° C. while 174 mL 2.5M n-butyl lithium (0.435 moles, 3 eq) was added dropwise. A precipitate formed and the slurry was allowed to warm to −5° C., then it was recooled to −70° C. 45 mL anh. Dimethyl formamide (0.581 moles, 4 eq) was added dropwise and the mixture was stirred at −70° C. for 30 minutes. The mixture was allowed to warm to room temperature and quenched by the addition of 300 mL sat. aq. NH₄Cl. The layers were separated and the aqueous layer was extracted with 300 mL ether. The combined organic layers were washed with water and brine then dried (MgSO₄) and concentrated in vacuum to give 57.55 grams of a red oil. This was chromatographed on Silica Gel using 40% EtOAc/Hexanes followed by EtOAc to give 25.56 grams of a red oil (61%). 1H NMR (Acetone-d6): 9.72 (s, 1H), 7.48 (d, 1H), 6.89 (d, 1H), 6.59 (s, 1H), 4.46 (t, 2H), 3.7 (t, 2H), 3.4 (m, 4H), 1.7 (m, 2H), 1.3 (q, 2H), 1.1 (t, 3H), 0.85 (t, 3H). MS (M+): 289.

Scheme 11.

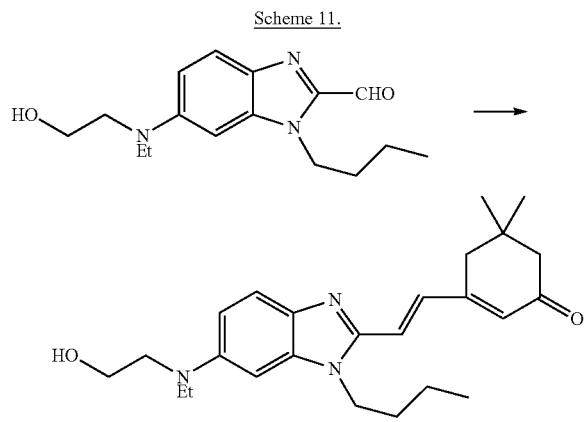

Example 37

The preparation of (E)-3-(2-(1-butyl-6-(ethyl(2-hydroxyethyl)amino)-1H-benzo[d]imidazol-2-yl)vinyl)-5,5-dimethylcyclohex-2-enone, shown in Scheme 11. A solution of 8.55 grams 2-((1-butyl-1H-2-formyl-benzo[d]imidazol-6-yl)(ethylamino)ethanol (29.5 mmoles) and 5.31 grams isophorone (38.4 mmoles) in 100 mL ethanol was added to a solution of 0.88 grams sodium (38 mmoles) in 100 mL ethanol. The mixture stirred overnight at room temperature then poured into 750 mL water. The solids were filtered off and washed with water to give 4.03 grams of a red solid (33%). The filtrate was extracted with 3×150 mL EtOAc. Those combined extracts were washed with brine then dried (MgSO₄) and concentrated in vacuum to give 9.82 grams of an oily red solid. The combined oily-red extract was triturated with 200 mL cold EtOAc to give 2.84 grams red solid (24%). The total yield was 57%. ¹H NMR (CDCl₃): 7.62 (dd, 2H), 6.88 (dd, 2H), 6.60 (s, 1H), 6.21 (s, 1H), 4.18 (t, 2H), 3.83 (m, 2H), 3.51 (m, 4H), 2.46 (s, 2H), 2.33 (s, 2H), 1.8 (m, 2H). 1.4 (m, 2H), 1.2 (m, 3H), 1.1 (s, 6H), 1.0 (t, 3H).

Scheme 12.

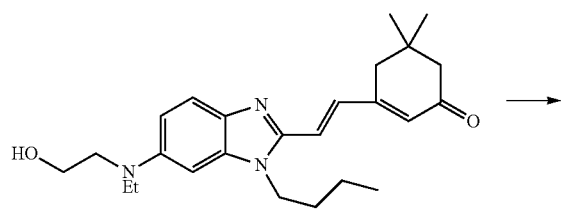

-continued

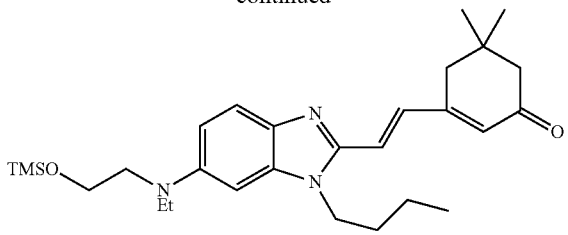

Example 38

The preparation of (E)-3-(2-(1-butyl-6-(ethyl(2-trimethylsiloxyethyl)amino)-1H-benzo[d]imidazol-2-yl)vinyl)-5,5-dimethylcyclohex-2-enone, shown in Scheme 12. A solution of 6.87 grams (E)-3-(2-(1-butyl-6-(ethyl(2-hydroxyethyl)amino)-1H-benzo[d]imidazol-2-yl)vinyl)-5,5-dimethylcyclohex-2-enone (16.8 mmoles) and 7 mL hexamethyldisilazane (34 mmoles, 2 eq) along with a few drops trimethylsilyl chloride was refluxed for 18 hours in 100 mL THF. The solution was cooled and concentrated in vacuum to give 8.72 grams of an orange solid. This was recrystallized from 75 mL hexanes to give 6.54 grams of orange crystals (81%). ¹H NMR (CDCl₃): 7.59 (dd, 2H), 6.85 (d, 1H), 6.81 (d, 1H) 6.45 (s, 1H), 6.20 (s, 1H) 4.16 (t, 2H), 3.77 (t, 2H), 3.50 (m, 4H), 2.46 (s, 2H), 2.32 (s, 2H), 1.8 (m, 2H). 1.39 (m, 2H), 1.2 (m, 3H), 1.12 (s, 6H), 0.97 (t, 3H), 0.1 (s, 9H).

Scheme 13.

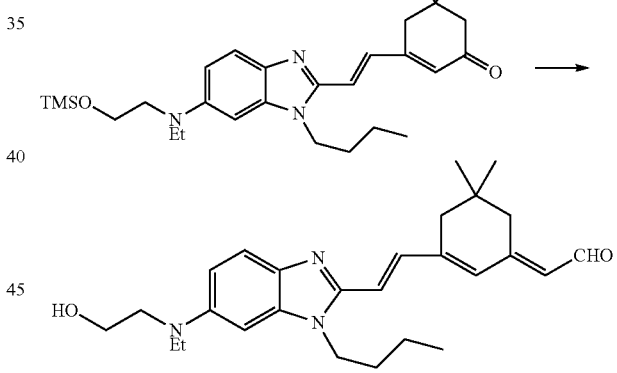

Example 39

The preparation of (E)-3-((E)-2-(1-butyl-6-(ethyl(2-hydroxyethyl)amino)-1H-benzo[d]imidazolo-2-yl)vinyl)-5,5-dimethylcyclohex-2-enylidene)acetaldehyde, shown in Scheme 13. A solution of 0.35 mL diisopropylamine (2.5 mmoles, 1.2 eq) in 10 mL THF was cooled to 0° C. while 1.0 mL 2.5M n-butyl lithium (2.5 mmoles, 1.2 eq) was added dropwise. After 15 minutes at 0° C. a solution of 0.32 grams N-ethylidenecyclohexamine (2.5 mmoles, 1.2 eq) in 5 mL THF was added. The solution was stirred for 15 minutes at 0° C. then added to a solution of 1.00 grams (E)-3-(2-(1-butyl-6-(ethyl(2-trimethylsiloxyethyl)amino)-1H-benzo[d]imidazol-2-yl)vinyl)-5,5-dimethylcyclohex-2-enone (2.1 mmoles) in 10 mL THF at −70° C. The solution was stirred for 60 minutes at −70° C. then 0.24 mL acetic anhydride (2.5 mmoles) was added. This was followed by 5 mL 2N HCl after 30 minutes. The solution was allowed to warm to room temperature then washed with brine, dried (MgSO$_4$) and concentrated in vacuum to give 1.20 grams of a dark red solid. This was chromatographed on Silica Gel using 3:1 EtOAC/hexanes followed by EtOAC to give 0.42 grams of a dark red solid (46%). 1H NMR (CDCl$_3$): 10.22 (d, 0.48H), 10.06 (d, 0.52H). MS (M+): 435.

The following prophetic example is for illustration purposes only and not to be used to limit any of the embodiments.

charge-transfer peak resonance ($\lambda_{max}$) shifts to longer wavelengths as the polarity of the solvent increases. The peaks of the absorption spectra of these BFFH dyes are not shifted to longer wavelengths when compared to the absorption spectra of the smaller tetraenic dyes that are similarly substituted, and which are reported in X.-H. Thou, J. Luo, S. Huang, T.-D. Kim, Z. Shi, Y.-Ju Cheng, S.-H. Jang, D. B. Knorr, Jr., R. M. Overney, A. K.-Y. Jen, Adv. Mater. 2009, 21, 1976-1981; and C. V. McLaughlin, L. M. Hayden, B. Polishak, S. Huang, J.

Scheme 14.

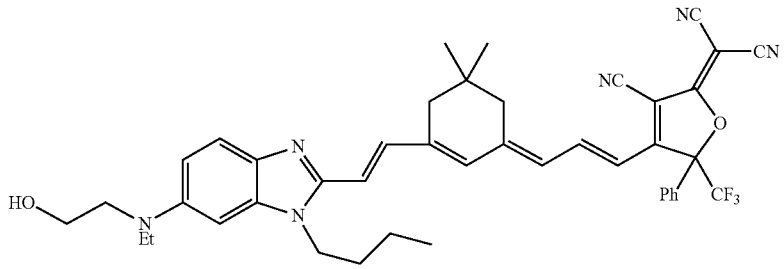

Example 40

The preparation of hydroxyl-functional benzimidazole dye, namely, 2-(4-((1E,3E)-3-(3-((E)-2-(1-butyl-6-(ethyl(2-hydroxyl)amino)-1H-benzo[d]imidazol-2-yl)vinyl)-5,5-dimethylcyclohex-2-enylidene)prop-1-enyl)-3-cyano-5-phenyl-5-(trifluoromethyl)furan-2(5H)-ylidene) malononitrile, shown in Scheme 14. To 25 mL ethanol is added (E)-3-((E)-2-(1-butyl-6-(ethyl(2-hydroxyethyl) amino)-1H-benzo[d]imidazolo-2-yl)vinyl)-5,5-dimethylcyclohex-2-enylidene)acetaldehyde (1.7 mmoles) and 0.79 grams 2-(3-cyano-4-methyl-5-phenyl-5-(trifluoromethyl)furan-2(5H)-ylidene)malononitrile (2.5 mmoles, 1.5 eq) [see Example 14 for the preparation of this compound]. This solution is stirred at room temperature while following the reaction by thin-layer chromatography, TLC (40% EtOAC/hexanes). In four hours the reaction is complete. The mixture is then concentrated in vacuum to give about 1.5 grams of a dark blue solid. This solid is then chromatographed on Silica Gel using 50% EtOAc/hexanes to give about 0.6 grams of a dark blue solid (about 45%).

Example 41

Figure 1B:
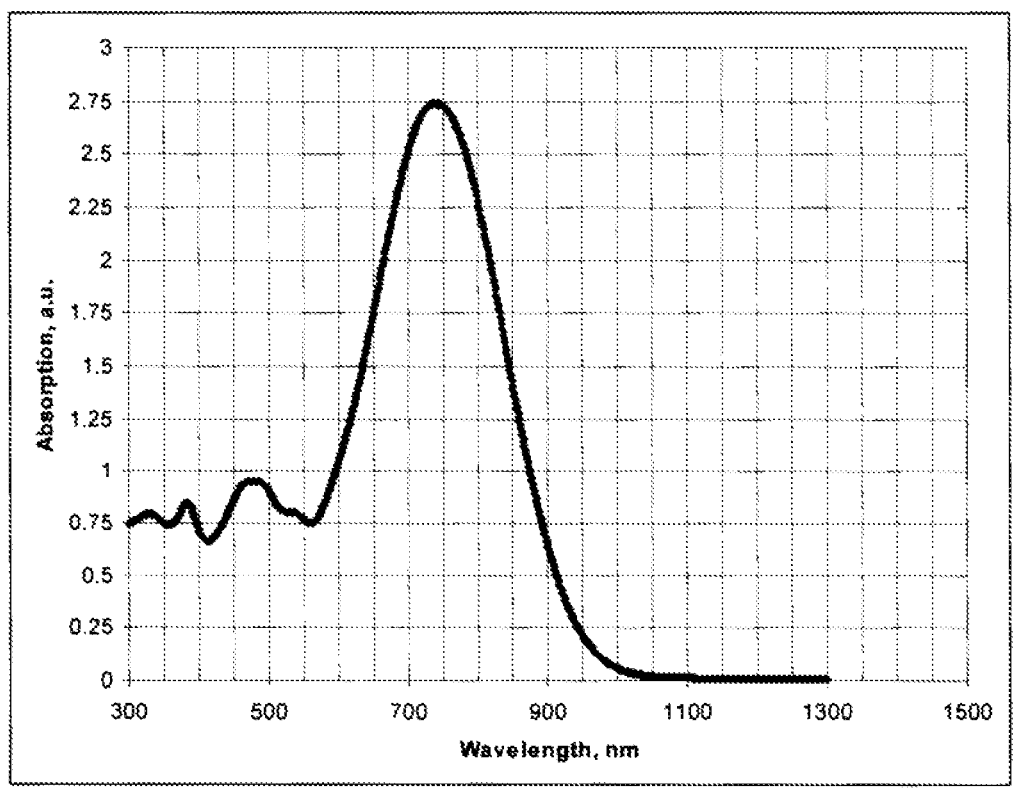
Figure 2:
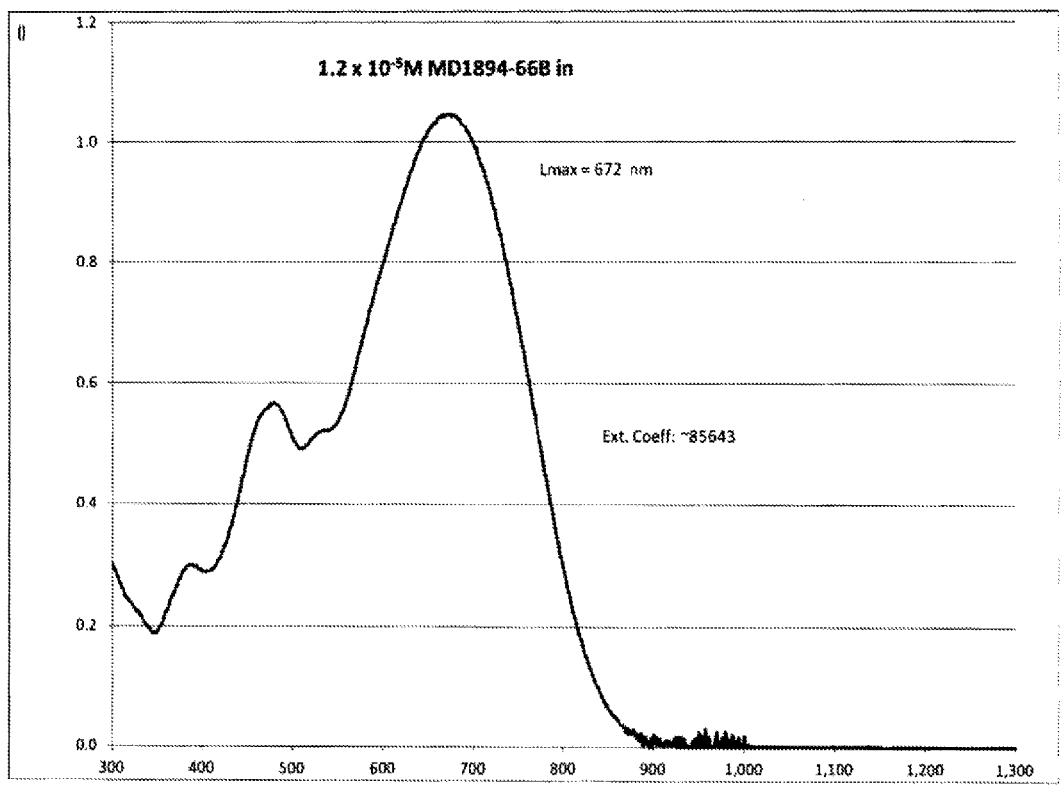
FIG. 2 is a graph of an example of the dye from Example 9, according to embodiments of the invention.

Optical absorption loss. The linear optical absorption properties of several BFFH dyes are shown in FIGS. 1a-b and 2 below. FIG. 1a is an example of the dye from Example 16. FIG. 1b is an example of the dye from Example 21. FIG. 2 is an example of the dye from Example 9. The UV-Vis spectra were measured with a Cary 5 spectrometer at room temperature. FIG. 1a is the UV-Vis spectrum of the benzofuran dye (dissolved in dioxane solvent) from working Example 16, which is similar to BFFH-11 in Table 1. FIG. 1b is the UV-Vis spectrum of the benzofuran dye (dissolved in toluene solvent) from working Example 21, which is similar to BFFH-10 in Table 1. FIG. 2 is the UV-Vis spectrum of the benzofuran dye (dissolved in toluene solvent) from working Example 9, which is similar to BFFH-1 in Table 1. The maxima of the absorption peaks ($\lambda_{max}$) are blue-shifted from the expected values for dyes with an extended pentaene framework.

The large absorption bands of these dyes are relatively narrow and monomodal indicating a lack of aggregation. The Luo, T.-D. Kim, A. K.-Y. Jen, Appl. Phys. Lett. 2008, 92, 151107. The fairly sharp cut-off at 1100 nm and the low extinction on the low-frequency side of the above spectra of these benzofuran dyes indicate that the optical absorption loss at 1550 nm will be quite acceptable for optical modulator applications.

The electro-optic properties of the BFFH-11 type of benzofuran chromophore, from working Examples 21, was demonstrated by dissolving this chromophore in a polycarbonate host material (a so-called guest-host material) and preparing films for the optical testing. Examples of film preparation and testing are described below.

Example 42

Method of film preparation. Cyclopentanone and dibromomethane were found to be good solvents for all of the dyes and polymers. These solvents have a useful volatility for the spin-casting and baking processes, and give films of high optical quality. Polymers and dyes were dissolved in separate solutions. Solutions were stirred with magnet bar until fully dissolved. The total-solids of the polymer solutions were 5-10 wt. %. A noted amount of dye solution was added to the polymer solution and stirred. Solutions were passed through a 0.2-μm PTFE Teflon® filter and allowed to sit ~3 h before spin-coating onto an ITO/glass slide (2000 rpm, 60 s with 500 rpm ramp). The slides were baked on a hot plate for 2 min at 90° C. The onset of thermal decomposition for these benzo-fused five-membered heterocyclic dyes was at about 160 to 180° C. as measured by Differential Thermal calorimetry, DSC, heating at 10°/min. Polymer films were cast including dye loadings of 30% to 50%. After solvent removal on a nitrogen-flushed heating plate, the absorption spectra of the dyes remained unchanged after aging at 120° C. for 20 min.

Example 43

Figure 3:
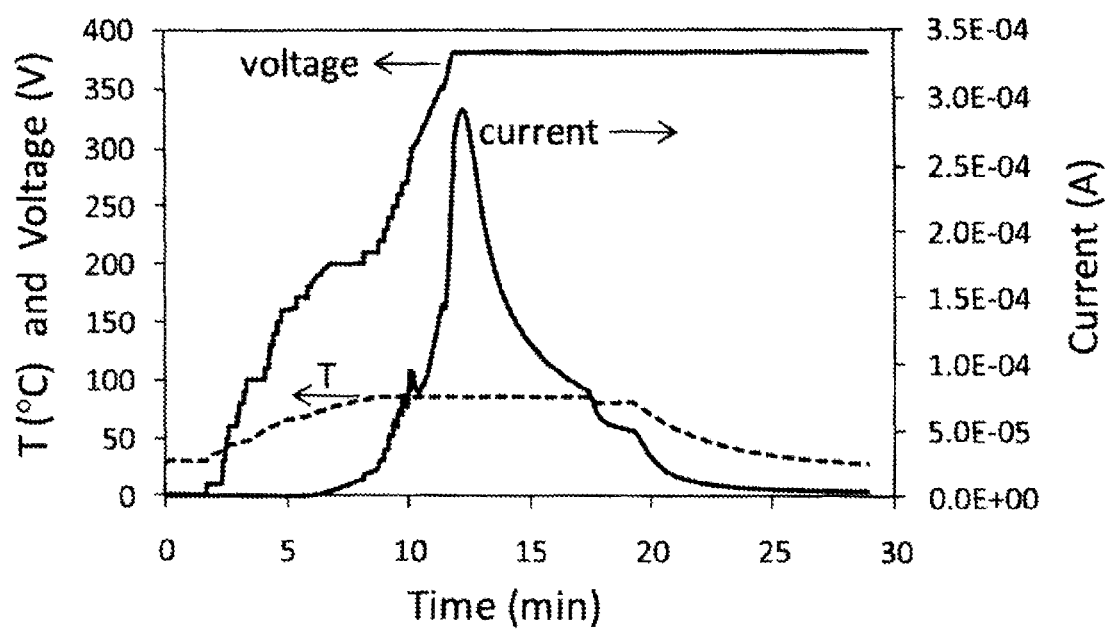
FIG. 3 is a graph illustrating details of a poling cycle, according to embodiments of the invention.

A method of electric-field poling of the films including the chromophores. A gold electrode (~100 nm thick) was deposited on the films using a thermal evaporator. Polar orientation of the dye in the guest-host films was achieved by contact poling. An FP90 control processor (Mettler Toledo, Inc.) was used to communicate with a FP82HT hot stage. The hot plate was enclosed in a nitrogen environment and poling was performed after the oxygen content decreased to less than ~200 ppm to avoid oxidation. A voltage source measurement unit (Keithley, Inc.) was used to apply up to 400 volts across the sample EO film. The details of a poling cycle are illustrated in FIG. 3. FIG. 3 shows a temporal profile of the temperature (in ° C., left axis), poling voltage (in volts, left axis), and the resulting current flowing through the film (in amperes, right axis) that was used to align the chromophores by electric-field poling. The temperature was increased close to the glass transition temperature (Tg) at a heating rate of −10° C./min and maintained for 5-10 min with 300-400 V (depending on the film thickness) applied across the sample film, following by cooling to room temperature with the field on.

Example 44

The optical method of measuring the $r_{33}$ electro-optic coefficient of poled films including the chromophores of embodiments of the invention. Teng-Man measurements were performed on the films to determine the electro-optic coefficients. To improve the estimates of $r_{33}$ from this method, error bars were calculated from the oscillating error curves as a function of film thickness by the method of Park and Herman [*Opt. Express* 2006, 14, 8866-8884].

Example 45

Results of the $r_{33}$ electro-optic coefficient measurements on guest-host films including the chromophores of embodiments of the invention. About 30% of the benzofuran-alkoxysiloxane dye, compound 16 shown in Scheme 2 above, was dissolved in a poly(vinyl butyral-co-vinyl acetate-co-vinyl alcohol) host polymer, and films were prepared according to Example 42 above. Electric-field poling was performed on this film according to Example 43 above, applying a maximum of 70 V/μm at 53° C. Using the optical measurement method in Example 44 above resulted in an $r_{33}$ value of 56±10 μpm/V at 1550 nm.

Example 46

A measurement of electro-optic coefficient ($r_{33}$) was performed on a guest-host film including 50% of the benzofuran-alkoxysiloxane dye, chromophore 16 in Scheme 2 above. A polycarbonate film including 50% of this dye was prepared according to Example 42 above. Electric-field poling was performed on this film according to Example 43 above, applying a maximum of 63 V/μm at 100° C. Using the optical measurement method in Example 44 above resulted in an $r_{33}$ value of 58±16 pm/V at 1550 nm.

The following prophetic examples are for illustration purposes only and not to be used to limit any of the embodiments.

Examples 47-50 describe preparations of BFFH dyes that include the 2,5-divinylene-heterocyclodiene unit in their π-conjugated framework. Two embodiments of the invention are described: one including the benzofuran unit, and one including the benzimidazole unit. Prior to each example, a scheme shows the reactants, intermediate precursor and/or dye prepared in that step.

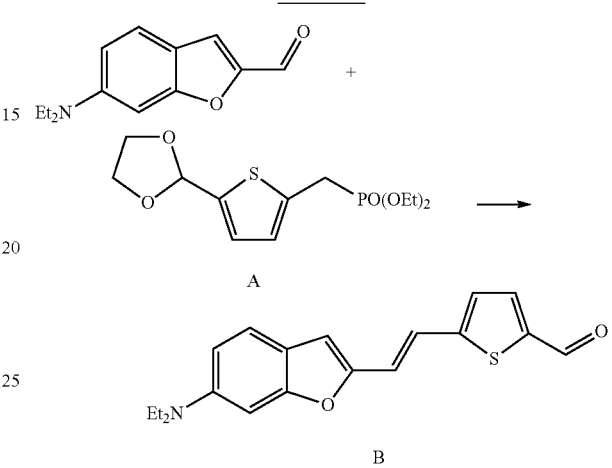

Scheme 15.

Example 47

6-Diethylaminobenzo[b]furan-2-carboxaldehyde (shown on left side of Scheme 15), which is prepared as in working Example 4, reacts with phosphonate A. The preparation of phosphonate A is that of Stenger-Smith et al. *J. Polym. Chem. A; Polym. Chem.* 2000, 38, 2824-2839. The two reactants in Scheme 15 are stirred in an organic solvent (including dimethyl formamide) in the presence of a base (including potassium t-butoxide) at elevated temperature (including 100° C.) until a reasonable yield of product is obtained (including 60% in 40 hours). The reaction mixture is hydrolyzed with acidic water. The aldehyde product B is purified by chromatography and gives the intermediate precursor B.

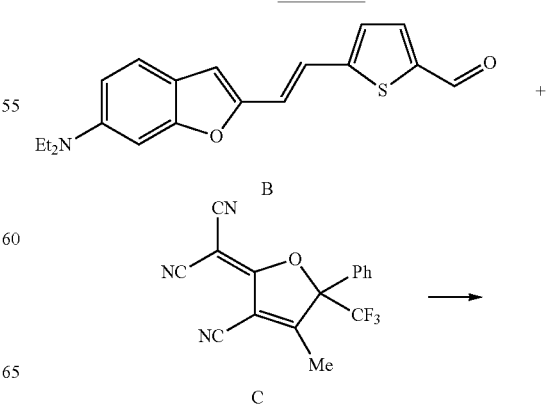

Scheme 16.

-continued

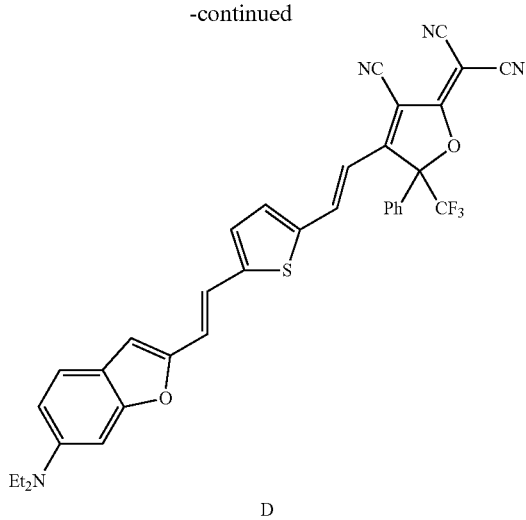

D

Example 48

As shown in Scheme 16, aldehyde B from Example 47 is reacted with electron-acceptor end group C, namely, 2-(3-Cyano-4-methyl-5-phenyl-5-(trifluoromethyl)furan-2-(5H)-ylideneymalononitrile (prepared as in Example 15). The two reactants in Scheme 16 are stirred in an organic solvent (including ethanol) in the presence of a base (including potassium t-butoxide) and refluxed under nitrogen. The reaction mixture is washed with water. The organic solvent is removed by rotary evaporation. The product D, a BFFH dye embodied in the invention, is chromatographed to purity.

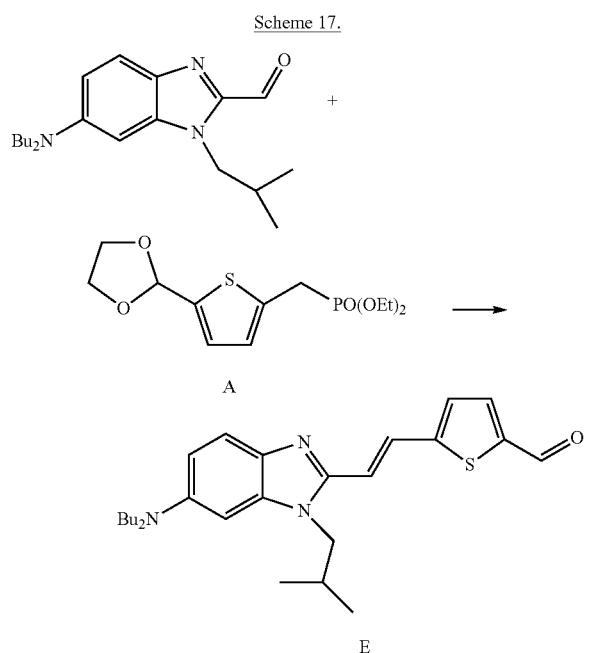

Example 49

6-(Di-n-butylamino)-1-iso-butyl-1H-benzimidazole-2-carboxaldehyde (shown on left side of Scheme 17), which is prepared as in working Example 26, reacts with phosphonate A. The preparation of phosphonate A is that of Stenger-Smith et al. *J. Polym. Chem. A; Polym. Chem.* 2000, 38, 2824-2839. The two reactants in Scheme 17 are stirred in an organic solvent (including dimethyl formamide) in the presence of a base (including potassium t-butoxide) at elevated temperature (including 100° C.) until a reasonable yield of product is obtained (including 60% in 40 hours). The reaction mixture is hydrolyzed with acidic water. The aldehyde product is purified by chromatography and gives the intermediate precursor E.

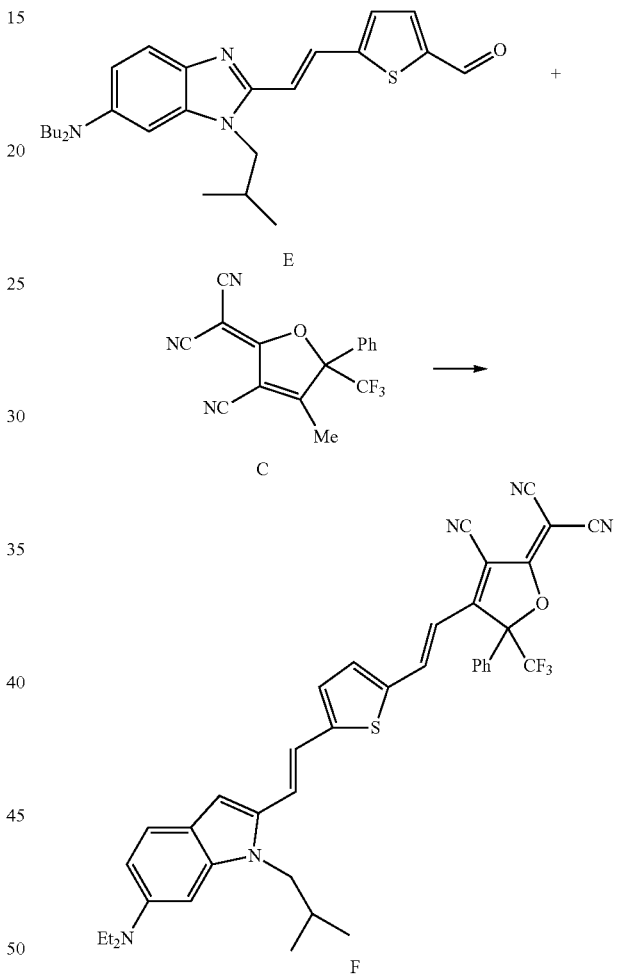

Example 50

As shown in Scheme 18, aldehyde E from Example 49 is reacted with electron-acceptor end group C, namely, 2-(3-Cyano-4-methyl-5-phenyl-5-(trifluoromethyl)furan-2-(5H)-ylidene)-malononitrile (prepared as in Example 15). The two reactants in Scheme 18 are stirred in an organic solvent (including ethanol) in the presence of a base (including potassium t-butoxide) and refluxed under nitrogen. The reaction mixture is washed with water. The organic solvent is removed by rotary evaporation. The product F, a BFFH dye embodied in the invention, is chromatographed to purity.

While the invention has been described, disclosed, illustrated and shown in various terms of certain embodiments or modifications which it has presumed in practice, the scope of the invention is not intended to be, nor should it be deemed to be, limited thereby and such other modifications or embodiments as may be suggested by the teachings herein are particularly reserved especially as they fall within the breadth and scope of the claims here appended.

What is claimed is:

1. A chromophore, comprising:
a base formula E;

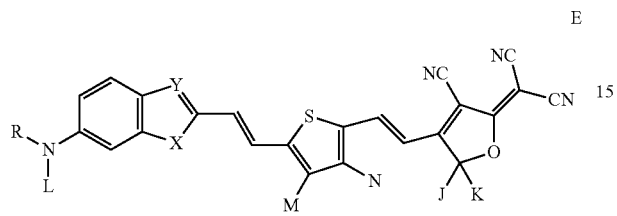

wherein X is selected from the group consisting of methylene, oxygen, sulfur, alkyl amine, amide, functionalized methylene, functionalized amine, and functionalized amide;
wherein Y is selected from the group consisting of carbon methine, functionalized carbon methine, azamethine, and atoms forming sp2-hybridized molecular orbitals;
wherein M and N are independently selected from the group consisting of hydrogen, fluorine, alkyl, aryl, alkoxy, aryloxy, t-butyldiphenylsiloxy, functionalized alkyl, functionalized aryl, functionalized alkoxy, functionalized aryloxy, and functionalized amide;
wherein J and K are independently selected from the group consisting of alkyl, aryl, functionalized alkyl, fluorine-functionalized alkyl, functionalized aryl, and fluorine-functionalized aryl; and
wherein R and L are independently selected from the group consisting of alkyl, aryl, functionalized alkyl, and functionalized aryl.

2. The chromophore of claim 1, wherein said X is oxygen, said Y is carbon ethane, wherein said M and said N are independently selected from the group consisting of alkyl, alkoxy and hydrogen.

3. The chromophore of claim 1, wherein said X is alkyl amine and said Y is azamethine.

4. The chromophore of claim 1, wherein said X is alkyl amine and said Y is carbon methine.

5. The chromophore of claim 1, wherein said X is sulfur and said Y is carbon methine.

6. An amorphous nonlinear optical material, comprising:
at least one chromophore having the base formula F;

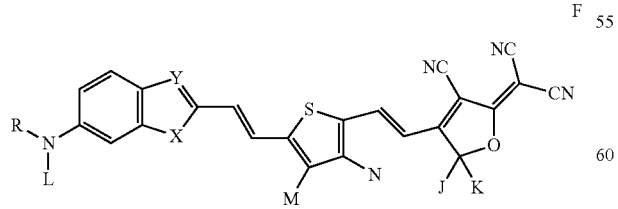

wherein X is selected from the group consisting of methylene, oxygen, sulfur, amine, amide, functionalized methylene, functionalized amine, and functionalized amide;
wherein Y is selected from the group consisting of carbon methine, functionalized carbon methine, azamethine, and atoms forming sp2-hybridized molecular orbitals;
wherein M and N are independently selected from the group consisting of hydrogen, fluorine, alkyl, aryl, alkoxy, aryloxy, t-butyldiphenylsiloxy, functionalized alkyl, functionalized aryl, functionalized alkoxy, functionalized aryloxy, and functionalized amide;
wherein J and K are independently selected from the group consisting of alkyl, aryl, functionalized alkyl, fluorine-functionalized alkyl, functionalized aryl, and fluorine functionalized aryl;
wherein R and L are independently selected from the group consisting of alkyl, aryl, functionalized alkyl, and functionalized aryl; and
wherein the concentration of said chromophore in said nonlinear optical material is greater than about $10^{18}$ molecules per cubic centimeter.

7. The material of claim 6, wherein the concentration of said chromophore in said nonlinear optical material is less than the concentration at which infrared light in the wavelength range of 1530 nm to 1570 nm becomes attenuated by more than about 0.25 decibels per millimeter of said nonlinear optical material.

8. The material of claim 7, wherein said X is oxygen and said Y is carbon methine.

9. The material of claim 7, wherein said X is alkyl amine and said Y is azamethine.

10. The material of claim 7, wherein said X is alkyl amine and said Y is carbon methine.

11. An electro-optical device, comprising:
at least one nonlinear optical material including at least one soluble chromophore having the base formula G;

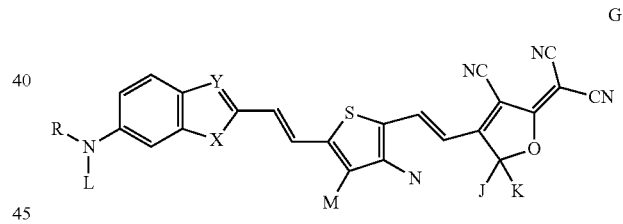

wherein X is selected from the group consisting of methylene, oxygen, sulfur, amine, amide, functionalized methylene, functionalized amine, and functionalized amide;
wherein Y is selected from the group consisting of carbon methine, functionalized carbon methine, azamethine, and atoms capable of forming sp2-hybridized molecular orbitals;
wherein M and N are independently selected from the group consisting of hydrogen, fluorine, alkyl, aryl, alkoxy, aryloxy, t-butyldiphenylsiloxy, functionalized alkyl, functionalized aryl, functionalized alkoxy, functionalized aryloxy, and functionalized amide;
wherein J and K are independently selected from the group consisting of alkyl, aryl, functionalized alkyl, and functionalized aryl; fluorine-functionalized alkyl, functionalized aryl, and fluorine-functionalized aryl;
wherein R and L are independently selected from the group consisting of alkyl, aryl, functionalized alkyl, fluorine-functionalized alkyl, functionalized aryl, and fluorine-functionalized aryl; and wherein the concentration of said chromophore in said nonlinear optical material is greater than about $10^{18}$ molecules per cubic centimeter.

12. The device of claim 11, wherein the concentration of said chromophore in said nonlinear optical material is less than the concentration at which infrared light in the wavelength range of 1530 nm to 1570 nm becomes attenuated by more than about 0.25 decibels per millimeter of said nonlinear optical material.

13. The device of claim 12, wherein said X being oxygen and said Y being carbon methine.

14. The device of claim 12, wherein said X is alkyl amine, said Y is azamethine, said M is hydrogen, and said N is hydrogen.

15. The device of claim 12, wherein said X is alkyl amine and said Y is carbon methine.

16. An electro-optical device, comprising:
at least one optical waveguide core formed by electric-field poling and including at least one soluble chromophore having the base formula H;

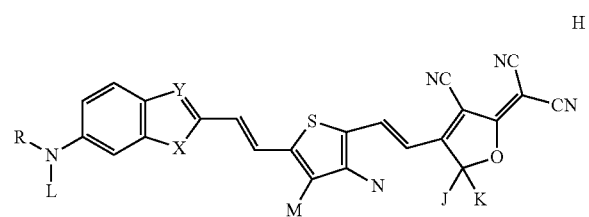

wherein X is selected from the group consisting of methylene, oxygen, sulfur, amine, amide, functionalized methylene, functionalized amine, and functionalized amide;

wherein Y is selected from the group consisting of carbon methine, functionalized carbon methine, azamethine, and atoms capable of forming sp2-hybridized molecular orbitals;

wherein M and N are independently selected from the group consisting of hydrogen, fluorine, alkyl, aryl, alkoxy, aryloxy, t-butyldiphenylsiloxy, functionalized alkyl, functionalized aryl, functionalized alkoxy, functionalized aryloxy, and functionalized amide;

wherein J and K are independently selected from the group consisting of alkyl, aryl, functionalized alkyl, fluorine-functionalized alkyl, functionalized aryl, and fluorine-functionalized aryl;

wherein R and L are independently selected from the group consisting of alkyl, aryl, functionalized alkyl, and functionalized aryl; and wherein the concentration of said chromophore in said nonlinear optical material is greater than about $10^{18}$ molecules per cubic centimeter.

17. The device of claim 16, wherein the concentration of said chromophore in said nonlinear optical material is less than the concentration at which infrared light in the wavelength range of 1530 nm to 1570 nm becomes attenuated by more than about 0.25 decibels per millimeter of said nonlinear optical material.

18. The device of claim 17, wherein said X is oxygen and said Y is carbon methine.

19. The device of claim 17, wherein said X is alkyl amine and said Y is azamethine.

20. The device of claim 17, wherein said X is alkyl amine and said Y is carbon methine.

* * * * *